United States Patent [19]

Wyborny et al.

[11] Patent Number: 5,127,404
[45] Date of Patent: Jul. 7, 1992

[54] TELEMETRY FORMAT FOR IMPLANTED MEDICAL DEVICE

[75] Inventors: Paul B. Wyborny, Fridley; Glenn M. Roline, Anoka; Lucy M. Nichols, Maple Grove; David L. Thompson, Fridley, all of Minn.

[73] Assignee: Medtronic, Inc., Minneapolis, Minn.

[21] Appl. No.: 765,475

[22] Filed: Sep. 25, 1991

Related U.S. Application Data

[63] Continuation of Ser. No. 468,407, Jan. 22, 1990, abandoned.

[51] Int. Cl.[5] .............................. A61N 1/08
[52] U.S. Cl. .................. 128/419 P; 128/903
[58] Field of Search ...... 128/419 P, 419 PG, 419 PT, 128/903

[56] References Cited

U.S. PATENT DOCUMENTS

| | | | |
|---|---|---|---|
| 3,962,697 | 6/1976 | Vreeland | 128/903 |
| 3,972,320 | 8/1976 | Kalman | 128/903 |
| 4,026,305 | 5/1977 | Brownlee et al. | 128/903 |
| 4,232,679 | 11/1980 | Schulman | 128/419 PG |
| 4,237,895 | 12/1980 | Johnson | 128/419 PG |
| 4,323,074 | 4/1982 | Nelms | 128/419 PG |
| 4,531,523 | 7/1985 | Anderson | 128/903 |

*Primary Examiner*—William E. Kamm
*Attorney, Agent, or Firm*—John A. Rissman; Harold R. Patton

[57] ABSTRACT

A method and apparatus are disclosed for telemetering both analog and digital data from an implantable medical device to an external receiver, such as between an implanted cardiac pacer and its external programming equipment. Analog data is first converted to digital format by an analog-to-digital converter, such that the transmission is digital data. A damped carrier at 175 kilohertz is pulse position modulated by the data. The modulation scheme defines a frame of slightly less than 2 milliseconds. The frame is divided into 64 individual time periods using a crystal clock. The data, along with synchronization and identification codes, are positioned into predefined ranges within each frame as measured by the individual time periods. The data is uniquely identified by the position of a burst of the carrier within the predetermined range. This modulation scheme enables necessary data to be transmitted at sufficiently high rates with reduced power requirements thereby conserving the internal battery of the implantable device. This modulation scheme provides flexibility of use, for example, with complex medical devices where transmission of increased volumes of data is desirable, such as cardiac devices having dual-chamber or multisensor capabilities, and for controlling particular conditions, such as tachyarrhythmia.

11 Claims, 8 Drawing Sheets

TELEMETRY FORMAT FOR IMPLANTED MEDICAL DEVICE

This application is a continuation of U.S. application Ser. No. 468,407, filed on Jan. 22, 1990, and now abandoned.

BACKGROUND OF THE INVENTION

1. Field of the Invention

The present invention generally relates to implantable medical devices, and more particularly, pertains to telemetry schemes for percutaneously transmitting analog and digital data from an implantable medical device.

2. Description of the Prior Art

The earliest implantable medical devices were designed to operate in a single mode and with no direct percutaneous communication. Later it became clinically desirable to vary certain of the operating parameters and change modes of operation. This was accomplished through the use of programmers and other external devices which transferred commands percutaneously to the implanted medical device.

The communication between the implant and the external world was at first primarily indirect. The operation of an implantable cardiac pacer could be observed, for example, in the electrocardiogram of the patient. Soon it became known that data could be sent from the implanted cardiac pacer by modulating the stimulation pulses in some manner. This can only provide a low bandpass channel, of course, without interfering with the clinical application of the device. Change of the pacing rate to indicate battery condition was a commonly used application of this technique.

As implantable cardiac pacers became more complex, the desirability to transfer more data at higher speeds resulted in the percutaneous transmission of data using a radio frequency carrier. The data to be transmitted is of two basic types, namely, analog and digital. The analog information can include, for example, battery voltage, intracardiac electrocardiogram, sensor signals, output amplitude, output energy, output current, and lead impedance. The digital information can include, for example, statistics on performance, markers, current values of programmable parameters, implant data, and patient and unit identifiers.

The earliest RF telemetry systems transmitted analog and digital information in separate formats, resulting in inefficient utilization of the available power/bandwidth. Also, these modulation schemes tended to be less than satisfactory in terms of battery consumption, and do not lend themselves to simultaneous transmission of differing data types.

Many types of RF telemetry systems are known to be used in connection with implantable medical devices, such as cardiac pacemakers. An example of a pulse interval modulation telemetry system used for transmitting analog and digital data, individually and serially, from an implanted pacemaker to a remote programmer is disclosed in U.S. Pat. No. 4,556,063 issued to Thompson et al., herein incorporated by reference. An example of a modern pacemaker programmer for use with programmable cardiac pacemakers having RF telemetric capabilities is disclosed in U.S. Pat. No. 4,550,370 issued to Baker, herein incorporated by reference. However, the telemetry format which is used under these systems, as well as other prior telemetry systems, have not been entirely adequate for reasons described above and a need for significant improvement has continued. As will become apparent from the following, the present invention satisfies that need.

SUMMARY OF THE INVENTION

The present invention percutaneously transmits all data from the implantable medical device in a digital format. It is pulse position modulated on an RF carrier. To accomplish this, the analog quantities must be converted to digital values either at the time of transmission, such as for real-time intracardiac electrocardiograms, or before storage in the memory of the device, as in the case of historical values of pacing rate for subsequent transmission for trend analysis.

Whether the data to be sent is initially analog or digital, it is transmitted in the same format, i.e., as digital information. The RF carrier is pulse position modulated to conserve battery energy. In this manner, only a short burst of the carrier, e.g., one cycle, is actually needed to transmit a given unit of data. The time position of that burst relative to a synchronizing standard determines the value of the data unit transmitted.

To accomplish this pulse position modulation, a frame of about 2 milliseconds is defined. Within this frame are positioned a synchronizing burst, a frame identifier burst, and one or more data bursts. The synchronizing burst is positioned at a fixed position in the frame. The frame identifier and data are variables, such that the corresponding bursts occur within a range of time within the frame. The range in which a burst is found defines the nature or type of the variable. The position in the range defines the value of the variable.

In particular, the present invention concerns a method and apparatus for performing telemetry of analog and digital data from an implanted medical device to an external programmer/receiver through the use of pulse position modulation technology and a framed digital data format.

In a preferred embodiment, a 175 Khz damped sinusoidal wave form pulse is generated at predetermined points within preselected sub-interval ranges of a very short time interval transmission data frame. In a single frame of approximately 2 milliseconds, for example, 8 bits of data may be rapidly transmitted, by delivering bursts of appropriately-timed pulse-positioned, radio frequency energy within the frame's sub-intervals consisting of: 1 frame-synchronizing bit; 1 data-identifier bit; and 2 data-value, sixteen-bit nibbles.

In one preferred embodiment, a method for transmitting information-encoded, telemetry signals percutaneously between an implanted medical device and an external device comprises the steps of:

(a) formatting the telemetry signal being transmitted using a frame having a predetermined time interval, the frame including at least first, second and third sub-interval ranges, each range comprising a set of available pulse positions;

(b) encoding the formatted telemetry signal by:
  (1) placing a frame-synchronizing signal at a predetermined pulse position within the first sub-interval to synchronize the frame;
  (2) placing an data-identifier signal at a predetermined pulse position within the second sub-interval to identify the type of information being transmitted;
  (3) placing a data-value signal at a predetermined pulse position within the third sub-interval to indicate the value of the information being transmitted; and (c) transmitting the formatted, encoded telemetry signals between the implanted medical device and the external device.

In another preferred embodiment, an apparatus for transmitting information-encoded, telemetry signals percutaneously between an implanted medical device and an external device comprises:

(a) a data bit source for bits corresponding to data to be transmitted;

(b) a frame formatter to define a transmission frame having a predetermined time interval including first, second and third sub-intervals;

(c) a clock to provide clock signals at preset clock intervals;

(d) a data encoder responsive to the clock and data bit source and coupled to the frame formatter, to encode the formatted telemetry signal by generating a signal at a certain pulse position within each of the first, second and third sub-intervals, such that the respective position of each signal within each sub-interval signifies its unique respective functions, namely, frame synchronization for the first sub-interval, data-type identification for the second sub-interval, and data-value indication for the third sub-interval; and (e) a communication system for transmitting the formatted, encoded telemetry signals between the implanted medical device and the external device.

Because all data transmission is in a digital format, great flexibility is achieved with regard to additional units of data for future applications. The use of the standardized format and capability of encoding more data into a single pulse also decreases the overall battery current requirements and serves to level the energy demand over time. Transmitting the analog data in digital form provides enhanced noise immunity and accuracy.

The transmission protocol provides data rates which are sufficient to transfer clinically useful EGM information in real time. Because each frame is independent, data quantities of varying precision can be transmitted using the same protocol. This modulation scheme provides flexibility of use, for example, with complex medical devices where transmission of increased volumes of data is desirable in real time, such as cardiac devices having dual-chamber or multisensor capabilities, and for controlling particular conditions such as tachyarrhythmia.

BRIEF DESCRIPTION OF THE DRAWINGS

The present invention will be better understood, and its attendant advantages will be readily appreciated, by reference to the accompanying drawings when taken in consideration with the following detailed description, wherein.

DETAILED DESCRIPTION OF THE PREFERRED EMBODIMENTS

A preferred embodiment of the present invention is disclosed relating to use of the improved telemetry format with an implantable cardiac pacer, which may be programmable. However, those of skill in the art will be readily able to adapt the teachings found herein to other implantable medical devices. It will also be understood by those of skill in the art that the telemetry format taught herein can be used for bi-directional communications between an implanted medical device and an external device.

Figure 1:
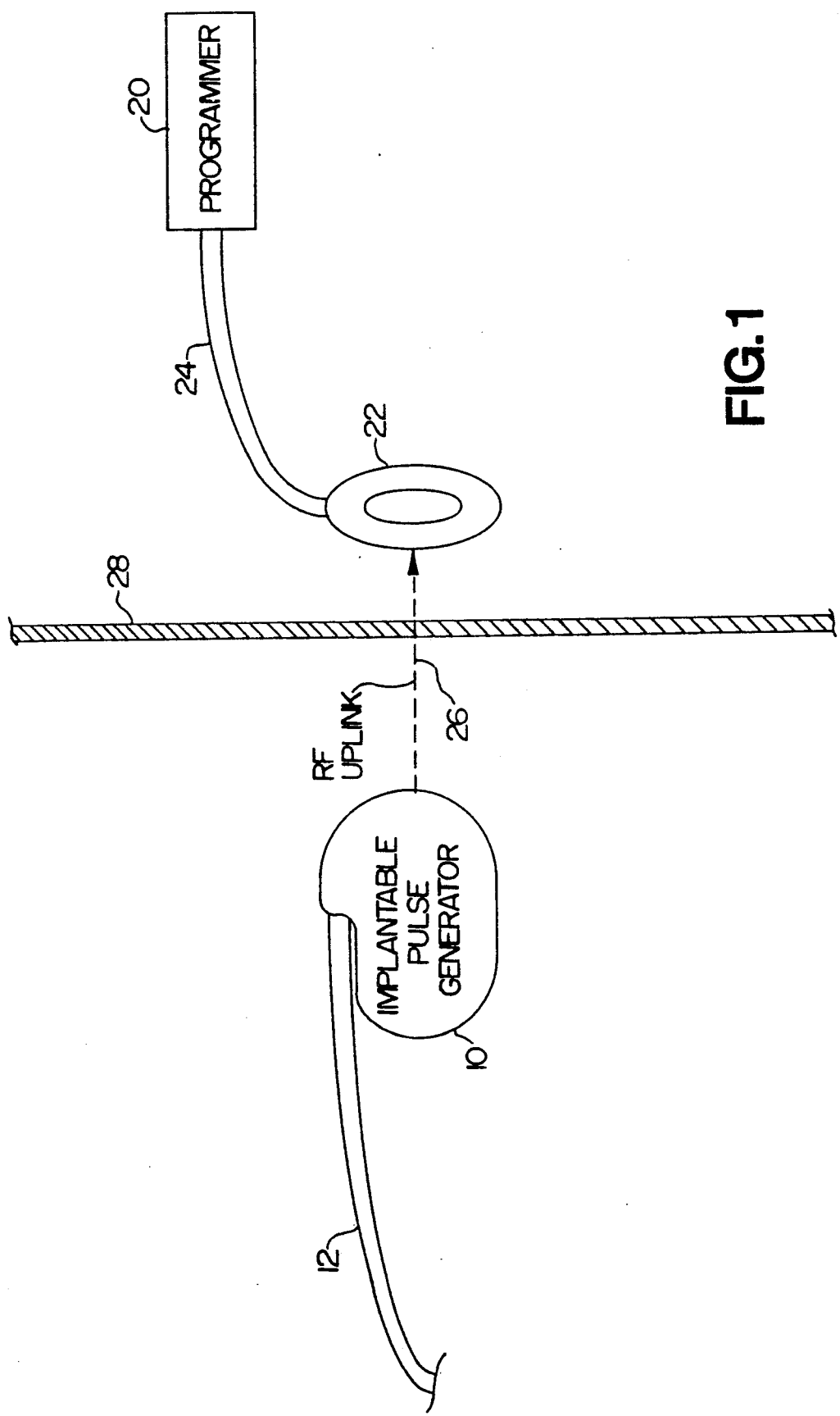
FIG. 1 is a simplified schematic view of an implantable medical device employing the improved telemetry format of the present invention.

FIG. 1 is a simplified schematic diagram of the present invention as employed in a cardiac pacing system. An implantable pulse generator 10 is implanted in the patient under the outer skin barrier 28. Implantable pulse generator 10 is electrically coupled to the heart of the patient using at least one cardiac pacing lead 12 in a manner known in the art. Percutaneous telemetry data is transmitted from implantable pulse generator 10 by an RF uplink 26 utilizing the improved telemetry format to a receiving antenna 22, which is coupled to a programmer 20 via a cable 24. Receiving antenna 22 also contains a magnet which activates a reed switch in implantable pulse generator 10 as a safety feature, as taught in U.S. Pat. No. 4,006,086 issued to Alferness et al., herein incorporated by reference. The telemetry data is demodulated and presented to the attending medical personnel by programmer 20.

Figure 2:
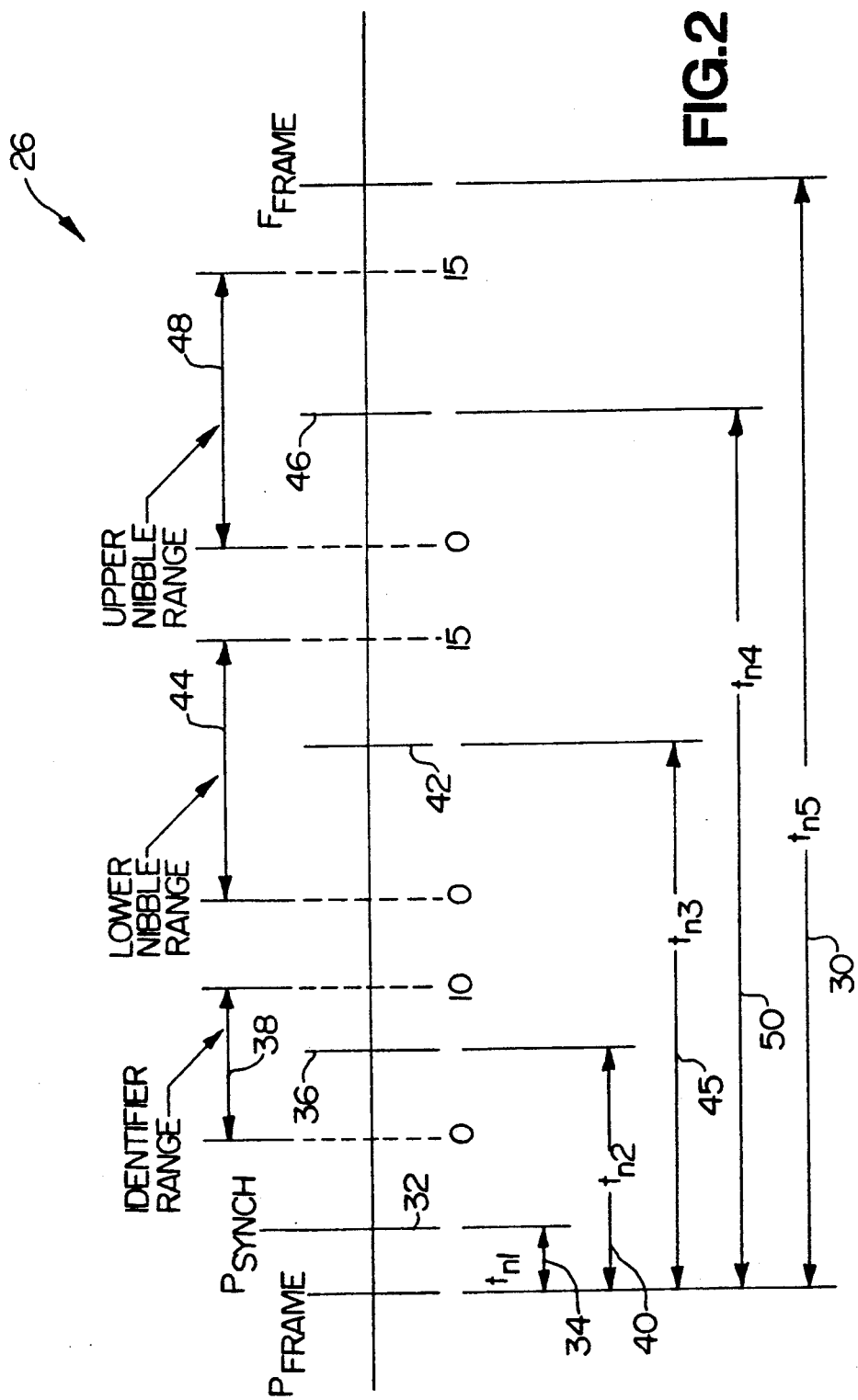
FIG. 2 is a conceptual view of one frame of the improved telemetry format of the present invention.

FIG. 2 is a schematic diagram of the protocol of RF uplink 26 using the improved telemetry format. The uplink uses a damped 175 kilohertz RF carrier which is pulse position modulated, as described in detail below. Shown at 30, the basic timing unit of the format is a frame, having a duration of $t_{n5}$. It will be understood by those skilled in the art, however, that the present invention can be practiced using fixed-length frames having periods of shorter or longer duration. In the preferred embodiment, the main timing source of implantable pulse generator 10 comprises a standard 32.768 kilohertz crystal clock which provides a basic clock cycle of 30.52 microseconds. Thus, a frame comprised of 64 clock cycles and extending over a fixed time interval of 1.953125 milliseconds is a convenient frame period, since such frame period is a binary multiple of the basic clock cycle.

A unique synchronizing signal is positioned within a first fixed range of each frame 30. This signal comprises a synchronizing RF pulse 32 which is located at a time $t_{n1}$ within frame 30. To properly function as a synchronizing pulse, it must be located at a fixed point within the first fixed range of frame 30, as shown at 34.

A four-bit frame identifier code is positioned within a second fixed range of each frame 30, such second fixed range comprising an identifier range 38. Identifier range 38 uses a total of eleven basic clock cycles as shown.

This identifier code comprises an identifier RF pulse 36 which is pulse position modulated within the identifier range 38. The position of identifier pulse 36 within identifier range 38 identifies the nature or type of data found within each frame 30 which is being transmitted, such as peak sense, peak pressure, sense threshold and others, as described in further detail below. Shown at 40, time interval $t_{n2}$ thus uniquely represents the value of identifier pulse 36, which value in turn identifies the data type being transmitted within frame 30.

Each frame 30 transfers one eight-bit byte of data along with the identifier code. This data is divided into two portions comprised of four bits of data each. A first portion of this data, namely the four least significant bits of the data byte, is positioned within a third fixed range of frame 30, such third fixed range comprising a lower nibble range 44. A second portion of this data, namely the four most significant bits of the data byte, is positioned within a fourth fixed range of frame 30, such fourth fixed range comprising an upper nibble range 48.

A lower nibble pulse 42 is pulse position modulated within lower nibble range 44, such that its value is uniquely identified by its location, such as at a time $t_{n3}$ shown at 45. An upper nibble pulse 46 is also pulse position modulated within upper nibble range 48, such that its value is uniquely identified by its location, such as at a time $t_{n4}$ shown at 50. Lower nibble range 44 and upper nibble range 48 each comprise sixteen basic clock cycles, permitting each of the sixteen unique values of the four-bit nibble to be specified. To prevent data overlap, suitable guardbands are positioned between each of the ranges within the frame to uniquely identify the synchronizing pulses, thereby avoiding undefined and erroneous data transmission.

Figure 3:
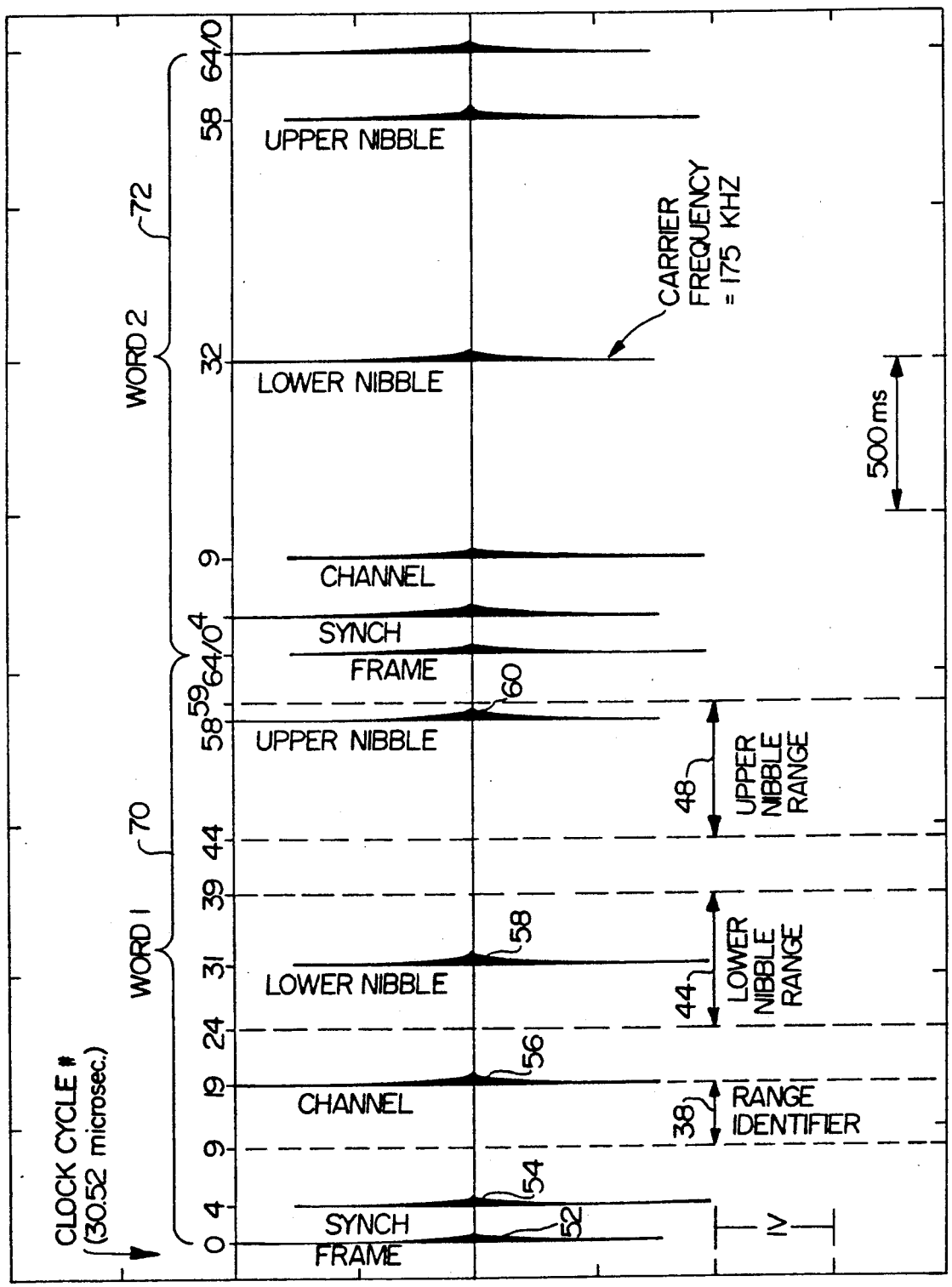
FIG. 3 is a view of the actual transmission pattern of two frames of the improved telemetry format.

FIG. 3 is a diagram of two frames of RF uplink 26, wherein a first frame corresponds to Word 1 shown at 70, and a second frame corresponds to Word 2 shown at 72. A count of clock cycles is indicated along an upper horizontal axis of this diagram for each frame. Each basic clock cycle has a duration of 30.52 microseconds. The first frame at 70 is initiated by an RF pulse 52. A synchronizing RF pulse 54 is shown uniquely identified as precisely four clock cycles later. Because the guardbands are all greater than four clock cycles, no combination of a frame identifier and data can appear as a synchronizing pulse. Synchronizing pulse 54 is used to provide frame synchronization between the transmitter (i.e., implantable pulse generator 10) and the receiver (i.e., programmer 20).

An identifier RF pulse 56 is located within identifier range 38, which range is defined as nine to nineteen basic clock cycles from the beginning of frame 70. In Word 1, for example, identifier pulse 56 is located at clock cycle nineteen. This identifies the frame as a particular type of data transfer, namely, "Sense Threshold" as indicated in Table 1 below.

TABLE 1

| Position | Identification |
|---|---|
| 9 | Memory |
| 10 | Idle |
| 11 | EGM-1 |
| 12 | Markers |
| 13 | Peak Sense |
| 14 | Pressure Waveform |
| 15 | Peak dp/dt |
| 16 | Peak Pressure |
| 17 | Delta Capacitor Voltage |
| 18 | Activity Counts |

TABLE 1-continued

| Position | Identification |
|---|---|
| 19 | Sense Threshold |

A lower nibble RF pulse 58 is located within lower nibble range 44, which range is defined as twenty-four to thirty-nine basic clock cycles from the beginning of frame 70. In Word 1, for example, lower nibble pulse 58 is located at clock cycle thirty-one, specifying a binary value of seven on a scale of zero to fifteen. An upper nibble RF pulse 60 is located at clock cycle fifty-eight within upper nibble range 48, which range is defined as forty-four to fifty-nine basic clock cycles from the beginning of frame 70, and is demodulated in similar fashion.

Figure 4:
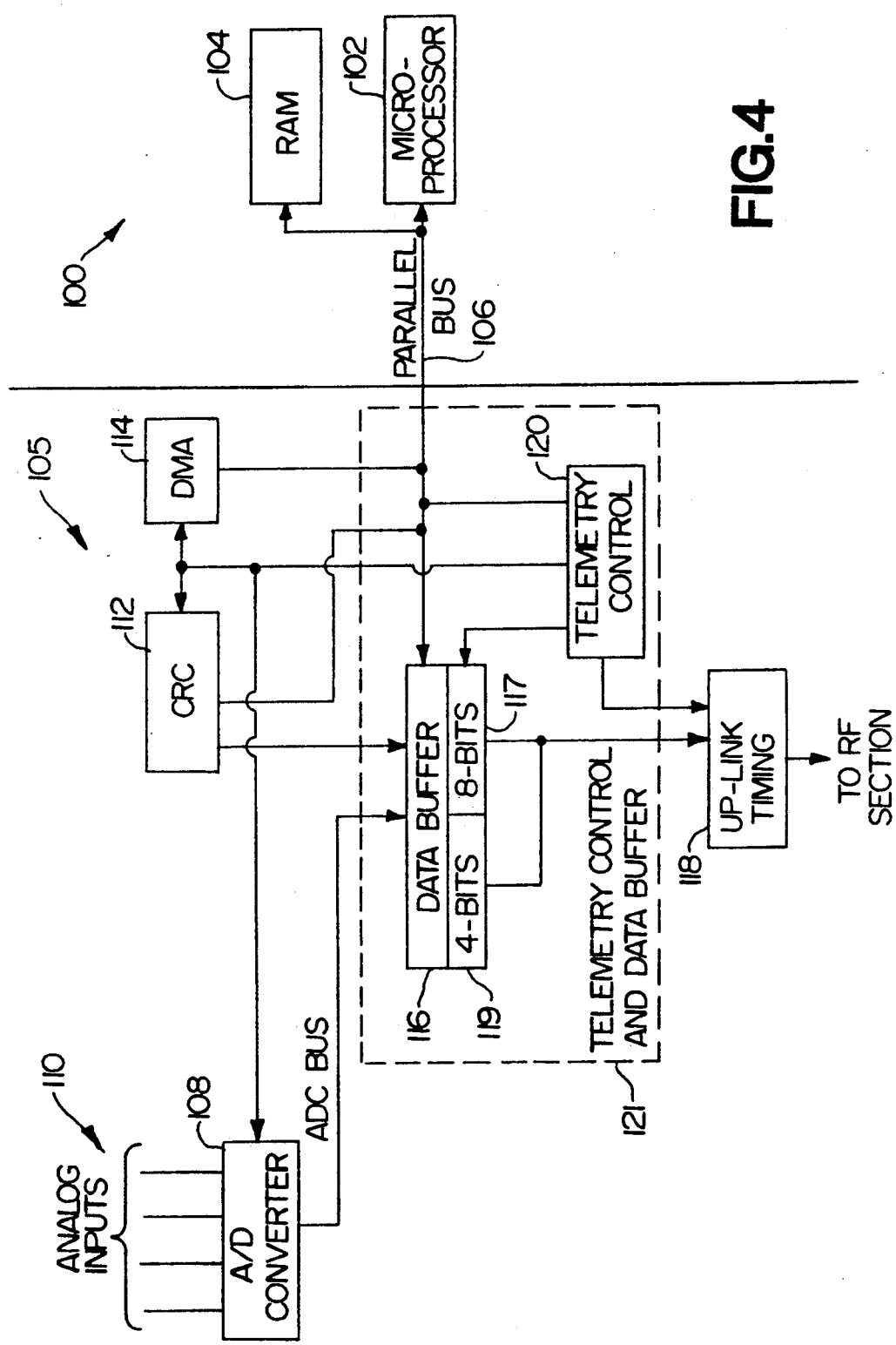
FIG. 4 is a block diagram of a portion of an implantable medical device for implementation of the improved telemetry format.

FIG. 4 is a block diagram of that portion of implantable pulse generator 10 which is associated with formatting and transmission of RF uplink 26. Most of the unique hardware which embodies the present invention is located on a single substrate, being a custom chip device indicated generally by arrow 105. The remainder is microprocessor-based logic indicated generally by arrow 100, comprising microprocessor 102, random access memory (RAM) 104, and parallel bus 106. The function of microprocessor-based logic 100 is described in further detail below.

Chip 105 has an analog-to-digital (A/D) converter 108 which receives a number of analog inputs 110 from a multiplexer (not shown). A/D converter 108 permits data to be transferred via RF uplink 26 to be digitized as necessary, so that all data is transmitted in a standardized digital form.

Circuitry (CRC) for generating and analyzing the cyclic redundancy code used to forward error detect telemetry data transmitted over RF uplink 26 is indicated at 112. In the preferred embodiment, it is also used for data received by implantable pulse generator 10 via a downlink (not shown). Circuitry (DMA) for providing direct memory access to RAM 104 is indicated at 114, thus permitting multiple byte transfers without constant management by microprocessor 102.

Key hardware used to implement RF uplink 26 comprises telemetry control and data buffer circuitry indicated generally within dashed lines at 121, which circuitry includes data buffer 116 and telemetry control 120, and up-link timing circuitry 118. Data buffer 116 includes storage for twelve bits of data. This storage is partitioned into a four-bit section 119 for storage of the frame identifier code, and an eight-bit section 117 for storage of the lower nibble and upper nibble of a frame. Data buffer 116 thus stores all of the variables for one complete frame. Data buffer 116 is used to stage the variables for the frame which may be received from RAM 104, A/D converter 108, CRC 12, or elsewhere along parallel bus 106.

Telemetry control 120 consists primarily of a telemetry status register. This register stores the telemetry commands and status as loaded by microprocessor 102. The contents of the register are thus used to gate the data at the proper time of the defined protocol.

Up-link timing 118 decodes the twelve bits of data stored in data buffer 116 to produce a set of timing signals which key bursts of RF energy at the appropriate times to pulse position modulate the 175 kilohertz carrier. Up-link timing 118 also keys bursts of RF energy at the fixed positions within the frame corresponding to the frame-initiating pulse and the synchronizing pulse.

Figure 5:
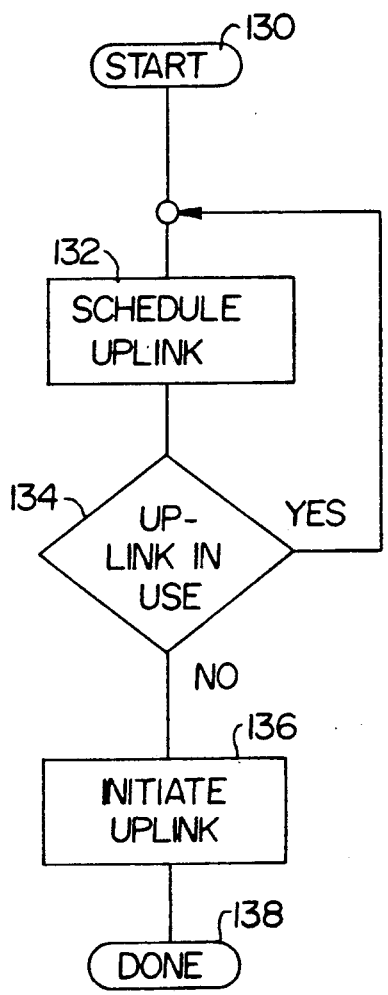
FIG. 5 is a simplified flowchart showing the basic function of software to perform the telemetry uplink operation of the improved telemetry format.

FIG. 5 is a basic flowchart showing the overall function of the microprocessor-based logic 100. The role is essentially one of initiation of the transfer, rather than management of each detail of the transmission. Software associated with RF uplink 26 is started at element 130, usually by a down-linked command to transfer data.

Element 132 schedules the requested transmission via the up-link facilities. This scheduling prioritizes uplink transmission requests. Lower priority is given to continuous real time transfers, such as EGM and battery voltage, whereas higher priority is given to single occurrence transmissions of status information.

After scheduling, element 134 determines whether an uplink transmission is currently in progress. If an uplink transmission is in progress, element 132 reschedules the request.

If an uplink transmission is not in progress after scheduling, element 136 initiates the uplink transmission by activating telemetry control 120. Exit is via element 138. While some additional management of the process is required during the transmission, a description of such further details has been omitted, since it is not believed necessary to one skilled in the art to fully understand the present invention. As to the software associated with the uplink transmission, however, a source code listing of the pertinent sections of such software has been attached hereto as Appendix A, and is incorporated by reference herein.

Figure 6:
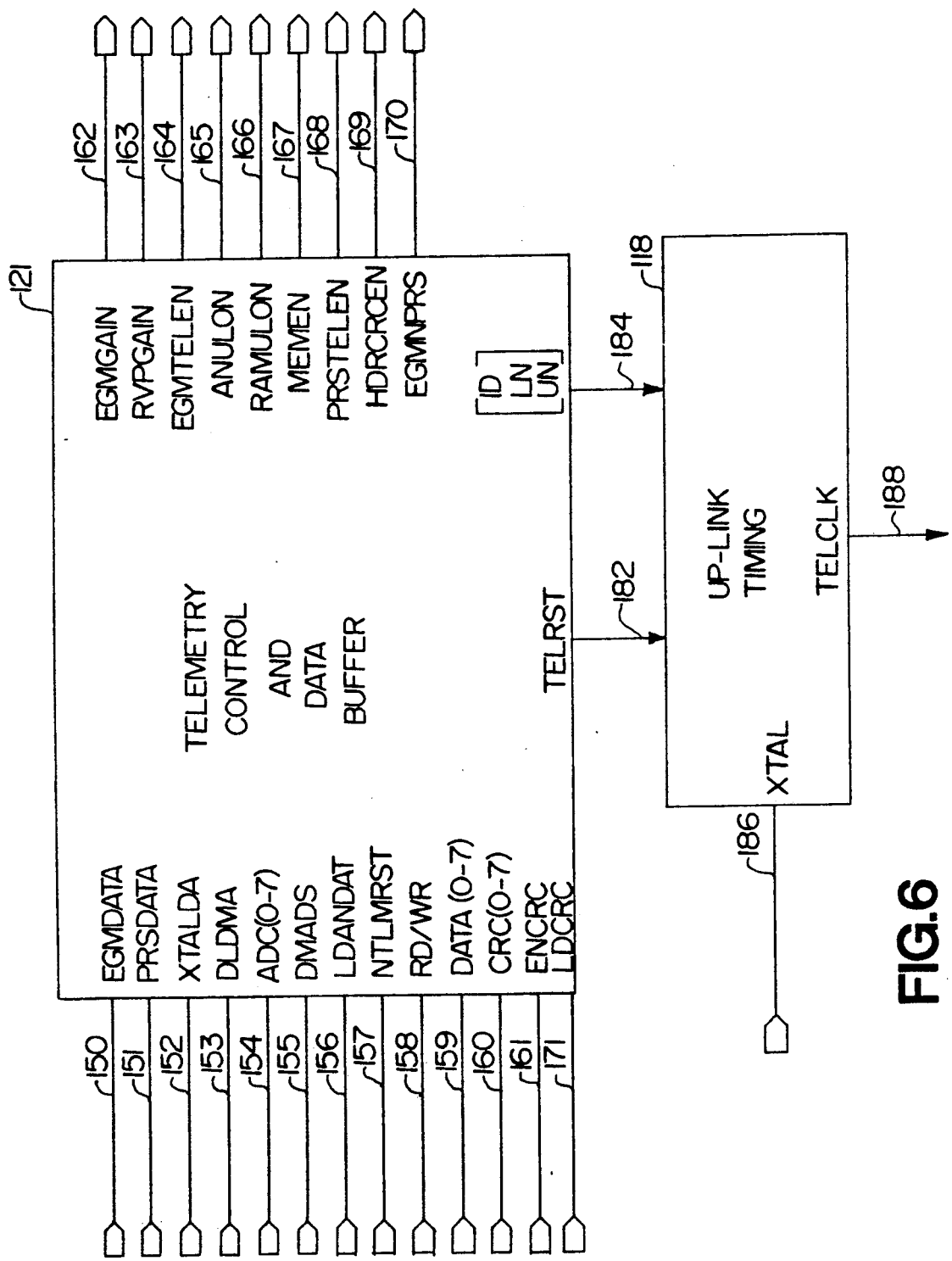
FIG. 6 is a block diagram of the circuitry of the telemetry uplink hardware for implementing the improved telemetry format.

FIG. 6 is a block diagram showing the major data and control signals of telemetry control and data buffer 121 (which includes data buffer 116 and telemetry control 120 shown in FIG. 4), and also of up-link timing 118. A primary function of data buffer 116, as indicated above, is the staging of the twelve variable bits of a given frame which correspond to a four-bit frame identifier ID, and dual-nibble data comprising a four-bit lower nibble LN and a four-bit upper nibble UN. The data is received over an eight-bit, parallel bus 159 and can be from any one of several sources. Control lines EGMDATA at 150, PRSDATA at 151, DLDMA at 153, DMADS at 155, LDANDAT at 156, ENCRC at 161 and LDCRC at 171 specify the source. The output of A/D converter 108 of FIG. 4 is presented separately to data buffer 116 as an eight-bit parallel transfer to ADC(0-7) at 154 (see FIG. 6). The output of CRC 112 is presented separately to data buffer 116 as an eight-bit parallel transfer to CRC(0-7) at 160, since those devices are located on the same substrate.

Telemetry control 120 outputs a number of control signals, including EGMGAIN at 162, RVPGAIN at 163, EGMTELEN at 164, ANULON at 165, RAMULON at 166, MEMEN at 167, PRSTELEN at 168, HDRCRCEN at 169 and EGMNPRS at 170. These control outputs are used to enable and control inputs to data buffer 116. The key outputs of telemetry control and data buffer 121 are TELRST at 182, which resets up-link timing 118 and initiates the beginning of a frame, and a parallel data transfer at 184, which transfers the frame identifier ID, lower nibble LN and upper nibble UN to up-link timing 118.

Up-link timing 118 receives the frame-initiating control signal TELRST at 182 and the parallel data transfer (ID, LN and UN) at 184. A primary function of up-link timing 118 is to key the transmission of 175 kilohertz RF energy at the proper times to indicate start of frame, frame synchronization, frame identifier, lower nibble and upper nibble. Timing for this function is provided by the 32.768 kilohertz crystal clock to up-link timing 118 with clock signal XTAL at 186. An output TELCLK is provided at 188 which keys the actual burst of RF carrier at the proper times.

Figure 7:
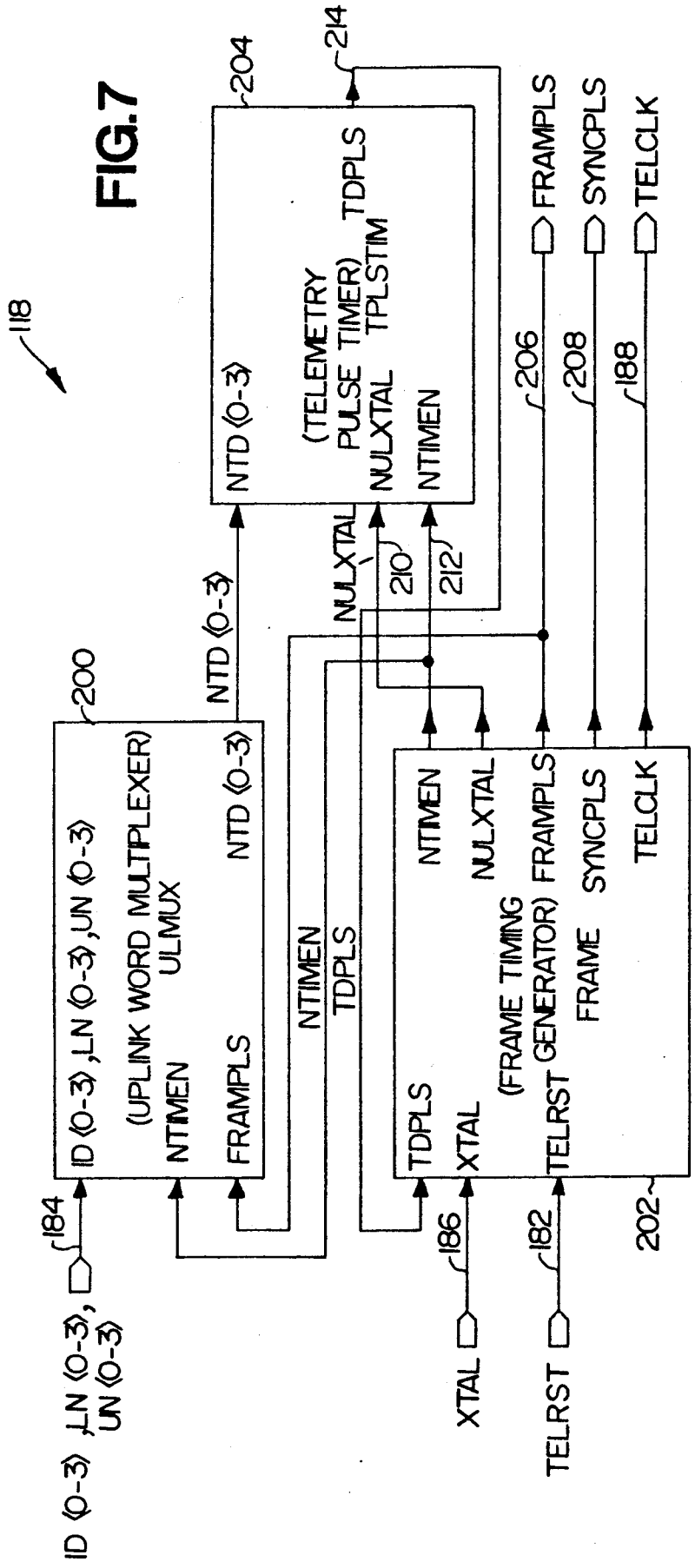
FIG. 7 is a block diagram of the circuitry of the telemetry timing for implementing the improved telemetry format.

FIG. 7 is a block diagram of up-link timing 118. A frame timing generator 202 provides the desired timing for a frame according to clock input XTAL at 186, in a manner hereinabove explained. Thus, each frame is comprised of sixty-four basic clock cycles. The process is initiated by receipt of the frame-initiating control signal TELRST at 182, which enables uplink when in a low state and disables uplink when in a high state. The initial clock cycle of a frame contains a burst of RF energy which is keyed by control signal TELCLK at 188, which is also used to trigger the start of the data decoding by an uplink word multiplexer 200.

After the proper four-bit quantity is selected (i.e., frame identifier ID first, lower nibble LN next, and upper nibble UN last), a telemetry pulse timer 204 determines the appropriate timing for a burst to be provided to frame timing generator 202, and a corresponding burst of RF energy is keyed. Each of the four-bit quantities thus results in the keying of a burst of RF energy at the appropriate time within each frame.

Figure 8:
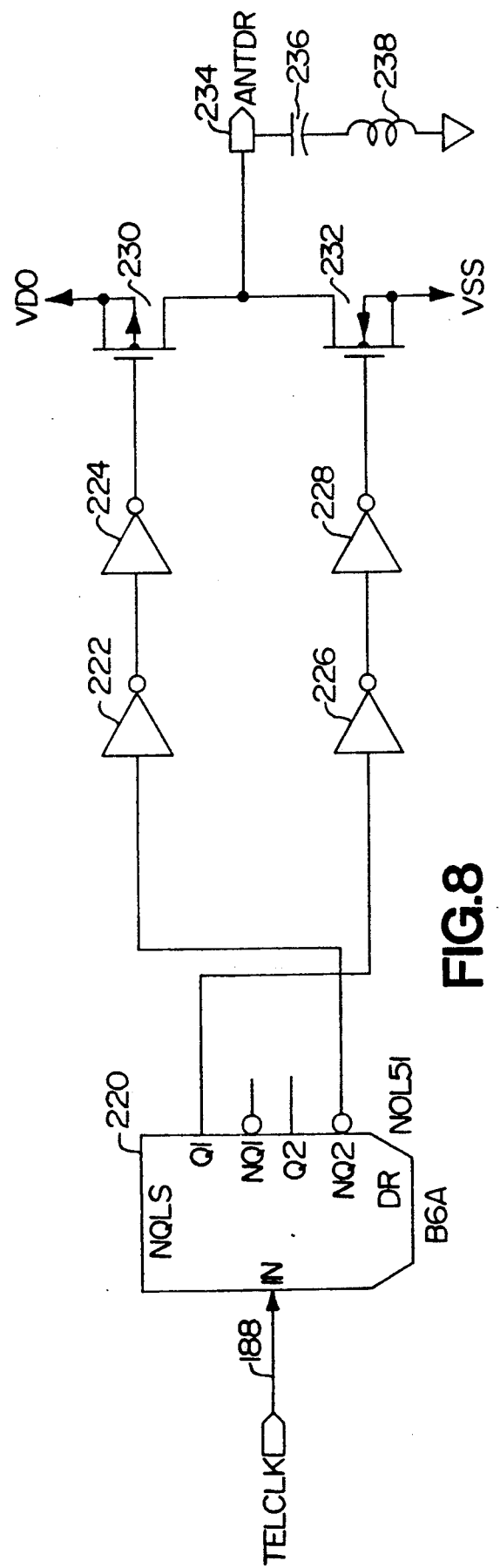
FIG. 8 is a schematic diagram of the driver circuitry for implementing the improved telemetry format.

FIG. 8 is a circuit diagram for the drive circuit for generating the RF carrier. A control signal TELCLK at 188 provides the timing information for keying the carrier. A non-overlap generator 220 functions as a delay device to save current by preventing output transistors 230 and 232 from conducting simultaneously. Every transition of control signal TELCLK at 188 causes one transition by non-overlap generator 220. Inverters 222, 224, 226 and 228 are scaled to provide efficient switching with sufficient drive to the gates of transistors 230 and 232. Transistors 230 and 232 drive the signal off of chip 105 to ANTDR at 234 to an antenna circuit. A tuned circuit of discreet components, capacitor 236 and coil 238, are located external to chip 105. Each transition thus causes this tuned circuit to resonate at 175 kilohertz, thereby generating one uplink burst.

While the invention has been described above in connection with the particular embodiments and examples, one skilled in the art will appreciate that the invention is not necessarily so limited. It will thus be understood that numerous other embodiments, examples, uses and modifications of and departures from the teaching disclosed may be made as to various other systems for telemetering data to and from an implantable medical device, without departing from the scope of the present invention as claimed herein.

APPENDIX A

```
Avocet 6805 Assembler v2.20, #01002   chip=146805
========== R2 SYSTEM DATA AREA ================= File: DATA.ASM
==========  $Revision:   3.0  $  ==============

=0005        400    ext_tlm_active    EQU   5      ;Extended telemetry is active
=0006        401    mag_state         EQU   6      ;Magnet state, mode and rate are
             402                                   ;set to VOO_MODE and mag_rate following
             403                                   ;permanent programming.
=0007        404    rr_trans          EQU   7      ;Rate response transition
             405
=00B0        406    TLM_NONMAG_MSK    EQU   10110000B  ;Mask to clear all telemetry
             407                                   ;flags except those associated
             408                                   ;with extended telemetry.
             409
             410   ;***********************************************************
             411   ;*              tlm2_flags
             412   ;***********************************************************
=0000        413    perm_prog_valid   EQU   0      ;Valid Permanent programming
             414                                   ;occurred.
=0001        415    reset_inhibit     EQU   1      ;Reset inhibit featured
             416                                   ;- used in validate message
=0002        417    reset_pace_trigger EQU  2      ;Reset pace trigger featured
             418                                   ;- used in validate message
=0003        419    pk_sense_rqst     EQU   3      ;Single Peak sense measurement
             420                                   ;requested from programmer
=0004        421    uplnk_cnfrm       EQU , 4      ;Uplink confirmation required
             422                                   ;on next event.
             423
             424   ;***********************************************************
             425   ;*              ULID
             426   ;***********************************************************
             427
=0005        428    CRC_error         EQU   5      ;CRC error indicator
=0006        429    uplink_memory     EQU   6      ;Uplink include memory block
=0007        430    uplink_CRC        EQU   7      ;Uplink includes CRC and header
             431
             432
```

```
433        ;***************************************************************
434        ;*                    Uplink_flags
435        ;***************************************************************
436
437  =0000  uplnk_disabled  EQU  0                ;Uplink is disabled
438  =0001  uplink_bsy      EQU  1                ;Uplink channel is busy
439  =0002  up_ram_pnd      EQU  2                ;RAM uplink pending
440  =0003  up_stat_pnd     EQU  3
441  =0004  intrrg_pnd      EQU  4                ;Interrogate data uplink pending
442  =0005  lcap_mrkr_pnd   EQU  5                ;Loss of capture marker uplink
443                                               ; pending
444  =0006  mrkr_pnd        EQU  6                ;Event marker uplink pending
445  =0007  meas_pnd        EQU  7                ;Measured value uplink pending
446
447  =0003  UPLNK_GN_SET    EQU  (2!^uplnk_disabled + 2!^uplink_bsy)
448                                               ;Disable uplink and set busy
449                                               ; for gain of signal
450        ;***************************************************************
451        ;*                    Uplink_stat equates
452        ;*
453        ;***************************************************************
454
455  =0004  page0_write     EQU  4                ;Write occured on page 0
456  =0005  magnet_applied  EQU  5                ;Reed switch is closed
457  =0006  checksum_error  EQU  6                ;Ram checksum error flag
458  =0007  POR_occured     EQU  7                ;POR flag
459
460  =00F0  UPLNK_CLR_MSK   EQU  11110000B        ;Clear error bits in uplink
461                                               ; stat
462  =00C0  UPLNK_POR_MSK   EQU  11000000B        ;Init mask used during POR
463
464        ;***************************************************************
465        ;*
466        ;*           Downlink Control Byte equates
467        ;*
```

```
;****************************************************************
;*
;*                    Telemetry equates
;*
;****************************************************************

;****************************************************************
;*                    Marker values
;*
;****************************************************************
=0066    MK_REFRAC_SENSE EQU    66H           ;Ventrical refractory sense mker
=00EE    MK_SENSE        EQU    0EEH          ;Ventrical sense marker
=00CC    MK_PACE         EQU    0CCH          ;Ventrical pace marker
=0077    MK_LOC          EQU    77H           ;Loss of capture marker
=00DD    MK_TRIGGERED    EQU    0DDH          ;Triggered pace marker =0080    UP_CRC          EQU    80H           ;Uplink CRC val for ULID regist
=0000    UP_NOCRC        EQU    0             ;Uplink no CRC val for ULID reg
=0040    UP_MEM          EQU    40H           ;Uplink mem val for ULID regist
=0000    UP_NOMEM        EQU    0             ;Uplink no mem val for ULID
                                              ;register ; ID code and CRC bits for uplink messages
;
=0080    STATUS_ID       EQU    0 + UP_CRC   + UP_NOMEM   ;Confirmation ID
=00C0    RAM_ID          EQU    0 + UP_CRC   + UP_MEM     ;RAM uplink ID
=0043    MARKER_ID       EQU    3 + UP_NOCRC + UP_MEM     ;Marker channel ID
=0044    PKSENSE_ID      EQU    4 + UP_NOCRC + UP_MEM     ;Measure value IDs
=0046    PKDPDT_ID       EQU    6 + UP_NOCRC + UP_MEM
=0047    PKPRESS_ID      EQU    7 + UP_NOCRC + UP_MEM
=0048    DLTAVOLT_ID     EQU    8 + UP_NOCRC + UP_MEM
=0049    ACTCNT_ID       EQU    9 + UP_NOCRC + UP_MEM
=004A    SENSTHRS_ID     EQU    10 + UP_NOCRC + UP_MEM
```

```
530  ;****************************************************
531  ;*            Misc. telemetry equates
532  ;****************************************************
533
534  ACCESS_CODE     EQU  0C3H          ;Telemetry access code for IPG
535  RM_MODEL_ID     EQU  10110011B     ;IPG model I.D. value, model 8444
536
537  INTRRG_SIZ      EQU  39            ;Size of interrogate block
538  MAX_MEMREAD     EQU  128           ;Maximum memory block read size
539
540  PG0             EQU  0FH           ;Control byte Page 0 ID
541  PG7             EQU  1             ;Control byte Page 7 ID
542  PG8             EQU  2             ;Control byte Page 8 ID
543  PG10            EQU  4             ;Control byte Page 10 ID
544
545  DNLK_EXTRA_LEN  EQU  3             ;Message overhead (sub from
546                                     ;HW bytcount)
547  DNLK_CB_INDX    EQU  1             ;First val field in downlink
548                                     ;message
549
550  ; Emergency values
551  ;
552  EMG_PW          EQU  31H           ;Emergency Pulse Width (2ms)
553  EMG_AMP         EQU  18H           ;Emergency pulse amplitude
554                                     ;(6.0 Volts)
555
556  HIGH_RATE       EQU  23H           ;Highest rate that will allow
557                                     ;full RAM uplink (170ppm)
558  UPLINK_DELAY    EQU  1EH           ;Minimum time before next
559                                     ;scheduled event
560                                     ;needed for RAM uplink (300ms)
561  UPSTAT_DELAY    EQU  03H           ;Minimum time before next
```

```
Avocet 6805 Assembler v2.20, #01002    Chip=146805
========== R2 EXECUTIVE =================== File: POREXEC.ASM
========== $Revision:  3.0  $ =========

;*********************************************************
;*                POR and Executive Macros               *
;*********************************************************

;@******************** CHECK_MARKER_UPLINK ***************
;@*
;@* Determine which marker code to uplink while in magnet mode or
;@* extended telemetry. If RAM uplink is in progress, the marker
;@* will be ignored.
;@*
;@* ENTRY CONDITIONS:
;@*   A pace/sense or refractory sensed event is being processed.
;@*   PACESTAT indicates if the event was refractory.
;@*
;@* EXIT CONDITIONS:
;@*   If maker channel is active and a valid marker is detected;
;@*   a marker is uplinked.
;@*
;@*********************************************************
;@ MACRO CHECK_MARKER_UPLINK
;@ BEGIN
;@    (* check for marker uplink *)
;@    IF (markers_active of mag_flags) THEN
;@    BEGIN
;------------------------------------------------------------
CHECK_MARKER_UPLINK %MACRO
CMU_START
           BRCLR   markers_active,mag_flags,CMU_END  ;Jump if marker channel NOT active
```

```
295  ;;@      IF ((refractory_evnt of PACESTAT)
296  ;;@          AND (sensed_evnt of exec_flags)) THEN
297  ;;@      BEGIN    (* Refractory sensed event *)
298  ;;@         IF ((timeout_int - event_time) > 1) THEN
299  ;;@            x := MK_REFRAC_SENSE;
300  ;;@         ELSE
301  ;;@            EXIT;
302  ;;@      END;
303  ;;@
304  ;;
305  ;         BRCLR   refractory_evnt,PACESTAT,CMU_VVT   ;Jump if NOT refractory sensed event
306  ;         BRCLR   sensed_evnt,exec_flags,CMU_VVT
307  ;         LDA     timeout_int
308  ;         SUB     event_time
309  ;         CMP     #1                  ;Is there enough time for marker uplink?
310  ;         BLS     CMU_END             ; No, just exit
311  ;         LDX     #MK_REFRAC_SENSE
312  ;         BRA     CMU_UL              ; Yes, load marker and go uplink it
313  ;
314  ;;
315  ;;@      ELSE IF ((paced_evnt of exec_flags) AND
316  ;;@          (sensed_evnt of exec_flags)) THEN
317  ;;@      BEGIN
318  ;;@         (* VVT mode, if triggered event send a triggered marker,
319  ;;@            unless output is inhibited then send sense marker. *)
320  ;;@
321  ;;@         IF NOT(inhibit of tlm_flags) THEN
322  ;;@            x := MK_TRIGGERED;
323  ;;@         ELSE
324  ;;@            x := MK_SENSE;
325  ;;@      END;
326  ;;
327  ;CMU_VVT
328  ;         BRCLR   paced_evnt,exec_flags,CMU_CKPACE   ;Jump if NOT both pace and sense
329  ;         BRCLR   sensed_evnt,exec_flags,CMU_CKPACE
330  ;                                     ;Check for output inhibited
331  ;
```

```
Avocet 6805 Assembler v2.20, #01002   chip=146805
========= R2 EXECUTIVE ================== File: POREXEC.ASM
=========  $Revision:   3.0  $  =========

332                    BRCLR    inhibit_enabled,tlm_flags,CMU_INHIBT
333                    LDX      #MK_SENSE         ;If not, get sense marker
334                    BRA      CMU_UL            ;Go uplink it
335   CMU_INHIBT
336                    LDX      #MK_TRIGGERED     ;Else get triggered marker
337                    BRA      CMU_UL            ;And send it
338   ;
339   ;@     ELSE IF ((paced evnt of exec_flags)
340   ;@             AND (NOT(inhibit of tlm_flags))) THEN
341   ;@        (* If pacing is not inhibited, send a PACE marker.  *)
342   ;@        x := MK_PACE;
343   ;
344   CMU_CKPACE
345                    BRCLR    paced_evnt,exec_flags,CMU_CKSENSE  ;Jump if NOT paced or if inhibited
346                    BRSET    inhibit_enabled,tlm_flags,CMU_CKSENSE
347                    LDX      #MK_PACE          ;Else get marker code
348                    BRA      CMU_UL            ;And send it
349   ;
350   ;@     ELSE IF (sensed evnt of exec_flags) THEN
351   ;@        x := MK_SENSE;
352   ;@     ELSE
353   ;@        (* No marker to uplink exit *)
354   ;@        EXIT;
355   ;
356   CMU_CKSENSE
357                    BRCLR    sensed_evnt,exec_flags,CMU_END   ;Jump if not sensed event
358                    LDX      #MK_SENSE         ;Else get marker value
359   ;
360   ;
361   ;@     (* Uplink marker code *)
362   ;@     CALLM UPLINK_MARKER(x);
363   ;@     END; (* marker channel active *)
364
365
```

```
366  ;----------------------------------------------------------------
367  ;CMU_UL
368  ;        UPLINK_MARKER              ;Ulink marker (value in x)
369  ;CMU_END
370         %ENDM
371  ;
372    @   END; (* CHECK_MARKER_UPLINK *)
373
374  $EJECT
375
       Avocet 6805 Assembler v2.20, #01002    chip=146805
       ========== R2 EXECUTIVE ================== File: POREXEC.ASM
       ==========  $Revision:   3.0  $ ==========

480  ;@************************* UPLINK_MARKER *************************
481  ;@*                                                               *
482  ;@* This macro uplinks event markers if the channel is free.      *
483  ;@*                                                               *
484  ;@* ENTRY CONDITIONS:                                             *
485  ;@*     This routine expects x to contain the marker value to be  *
486  ;@*     uplinked.                                                 *
487  ;@*                                                               *
488  ;@* EXIT CONDITIONS:                                              *
489  ;@*     If the uplink channel is available it is captured and the *
490  ;@*     marker is uplinked. If the channel is busy and there are  *
491  ;@*     no pending markers the marker is flagged pending for uplink *
492  ;@*     at the end of the current uplink.                         *
493  ;@*                                                               *
494  ;@***************************************************************
495
496  ;UPLINK_MARKER %MACRO
497  ;-----------------------------------------------------------------
498  ;@ MACRO UPLINK_MARKER;
499  ;@ BEGIN
500  ;@     disable interrupts;
501  ;@     (* Check if uplink channel is available.*)
502  ;@     IF NOT(uplink_disabled of uplink_flags) THEN
503  ;@         BEGIN
504
```

```
505         ;;@    IF NOT(uplink_bsy of uplink_flags) THEN
506         ;;@      BEGIN
507         ;;@        (* If uplink channel is free then uplink marker *)
508         ;;@        uplink_bsy of uplink_flags := TRUE;
509         ;;@        enable interrupts;
510         ;;@        marker_val := x;
511         ;;@        TELADHI := HIADDR(marker_val);
512         ;;@        TELADLO := LOADDR(marker_val);
513         ;;@        BYTCOUNT := 1;
514         ;;@        ULID := MARKER_ID;
515         ;;@        RAM_uplink of TELSTAT := TRUE;
516         ;;@      END;
517         ;------------------------------------------------------
518         ;UPM_START      SEI                              ;Disable interrupts
519                        BRSET    uplink_disabled,uplink_flags,UPLMDONE ;Jump if uplink disabled
520
521         ;UPLMARKER
522                        BRSET    uplink_bsy,uplink_flags,UPL_BSY      ;Jump if uplink BUSY
523
524         ;;      Uplink NOT busy
525         ;;
526         ;;
527                        BSET     uplink_bsy,uplink_flags     ;Flag uplink busy
528                        CLI                                   ;Enable interrupts
529                        STX      marker_val                   ;Put marker value in buffer
530                        LDA      #HIGH marker_val  ;Get MSB of buffer address
531                        STA      TELADHI                      ;Write it to hardware
532                        LDA      #LOW marker_val   ;Get LSB of buffer address
533                        STA      TELADLO                      ;Etc.
534
535                        LDA      #1
536                        STA      BYTCOUNT                     ;Get output count
537                                                              ;Write to hardware count register
538
539                        LDA      #MARKER_ID                   ;Get ID code
540                        STA      ULID                         ;Tell the hardware
541
542                        BSET     RAM_uplink,TELSTAT           ;Start the uplink
543                        BRA      UPLMDONE
544
```

```
545           ;:@         ELSE
546           ;:@         BEGIN
547           ;:@

Avocet 6805 Assembler v2.20, #01002    Chip=146805
      ========= R2 EXECUTIVE ======================= File: POREXEC.ASM
      ========= $Revision:   3.0  $ ==========

548           ;:@                 (* If no markers are pending the flag one pending *)
549           ;:@                 mrkr_pnd of uplink_flags := TRUE;
550           ;:@                 marker_val := x;
551           ;:@              END;
552           ;:@           END;
553           ;:@           enable interrupts;
554           ;:@
555           ;:@
556           ;:  Uplink BUSY
557           ;:
558           ;:UPL_BSY
559                         BSET        mrkr_pnd,uplink_flags    ;Flag marker pending and
560                         STX         marker_val               ;store marker in the buffer
561
562           ;UPLMDONE
563                         CLI                                  ;Enable interrupts
564                         %ENDM
565
566           ;:@           END;   (* UPLINK_MARKER *)
567
568           $EJECT
569
```

```
Avocet 6805 Assembler v2.20, #01002   Chip=146805
========== R2 PACE OR SENSE MODULE ==============  File: POS.ASM
==========    $Revision:   3.0  $   ============
```

```
1816  ;@*********************** UPLINK_INTRRG ****************************
1817  ;@*                                                                *
1818  ;@*  This macro uplinks the interrogate block of size INTRRG_SIZ and *
1819  ;@*  starting at the address pointed to by INTRRG_AD if the uplink *
1820  ;@*  channel is free. Otherwise, if there is no RAM uplink, the    *
1821  ;@*  interrogate block is set pending and is scheduled via the next *
1822  ;@*  TELBF interrupt, occurring when the uplink channel becomes    *
1823  ;@*  free. All other uplinks have to be disabled while checking the *
1824  ;@*  uplink flags to avoid contention of the uplink channel.       *
1825  ;@*                                                                *
1826  ;@*  ENTRY CONDITIONS:                                             *
1827  ;@*      None.                                                     *
1828  ;@*                                                                *
1829  ;@*  EXIT CONDITIONS:                                              *
1830  ;@*      None.                                                     *
1831  ;@*                                                                *
1832  ;@*                                                                *
1833  ;@*****************************************************************
1834
1835  ;@MACRO UPLINK_INTRRG;
1836  ;@BEGIN
1837  ;@ (* Capture uplink channel - If busy set interrogate pending *)
1838  ;@ disable interrupts;
1839  ;@ IF NOT(uplnk_disabled of uplink_flags) THEN
1840
1841  UPLINK_INTRRG %MACRO
1842               SEI                           ;Dissable interrupts
1843               BRSET    uplnk_disabled,uplink_flags,UI_END
1844
1845  ;;@     BEGIN
1846  ;;@       IF NOT(uplink_bsy of uplink_flags) THEN
1847  ;;@       BEGIN
1848  ;;@         uplink_bsy of uplink_flags := TRUE;
1849  ;;@         enable interrupts;
```

```
1850  ;@                 statbyt := uplnk_stat;
1851  ;@                 CALLM LOAD_INTRRG_UPLINK WITHIN R2LIB;
1852  ;@                 RAM_uplink of TELSTAT := TRUE;
1853  ;@             END;
1854  ;-------------------------------------------------------------
1855                  BRSET    uplink_bsy,uplink_flags,UI_UBSY
1856                  BSET     uplink_bsy,uplink_flags
1857                  CLI                              ;Enable interrupts
1858                  LDA      uplnk_stat
1859                  STA      statbyt                 ;Initialize the uplink status byte
1860  UI_LIU          LOAD_INTRRG_UPLINK
1861  UI_LIU_END
1862                  BSET     RAM_uplink,TELSTAT
1863                  BRA      UI_END
1864  ;-------------------------------------------------------------
1865  ;@             ELSE
1866  ;@                 intrrg_pnd of uplink_flags := TRUE;
1867  ;@             END;
1868  ;-------------------------------------------------------------
1869  UI_UBSY         BSET     intrrg_pnd,uplink_flags
1870  ;-------------------------------------------------------------
1871  ;@             enable interrupts;
1872  ;-------------------------------------------------------------
1873  UI_END          CLI                              ;Enable interrupts
1874                  %ENDM
1875  ;@END;          (* UPLINK_INTRRG *)
1876  ;-------------------------------------------------------------
1877  $EJECT
1878
1879
        Avocet 6805 Assembler v2.20, #01002    Chip=146805
        ========= R2 LSCAP INTERRUPT MODULE ============ File: LOC.ASM
        =========  $Revision:  3.0  $  ============
409  ;@*********************** UPLINK_LCAP_MARKER *******************
410  ;@*                                                            *
```

```
411  ;@*  This macro uplinks loss of capture markers.
412  ;@*
413  ;@*  ENTRY CONDITIONS:
414  ;@*    Under magnet operations, the LSCAPINT interrupt is used for
415  ;@*    the uplink of LOC markers if the channel is free.
416  ;@*
417  ;@*  EXIT CONDITIONS:
418  ;@*    None.
419  ;@*
420  ;@*****************************************************************
421
422       MACRO UPLINK_LCAP_MARKER;
423   @   BEGIN
424   @
425   @     disable interrupts;
426   @     IF NOT (uplnk_disabled of uplink_flags) THEN
427
428  UPLINK_LCAP_MARKER %MACRO
429  ULM_START
430                SEI                        ;Disable interrupts
431  ULM_INT
432                                           ;Jump if NOT (NOT uplnk_disabled)
433                BRSET   uplnk_disabled,uplink_flags,ULM_DONE
434
435   @     BEGIN
436   @
437  ;;@       IF NOT(uplink_bsy of uplink_flags) THEN
438  ;;@
439                                           ;Jump if uplink busy
440                BRSET   uplink_bsy,uplink_flags,ULM_LCP
441
442   @       BEGIN
443   @
444  ;;@         (* If Uplink channel is free then uplink marker *)
445  ;;@         uplink_bsy of uplink_flags := TRUE;
446  ;;@         enable interrupts;
447  ;;@         TELADHI := HIADDR(LCAP_MARKER);
448  ;;@         TELADLO := LOADDR(LCAP_MARKER);
449  ;;@         BYTCOUNT := 1;
450  ;;@         ULID := MARKER_ID;
451
```

```
452  ;;@        RAM_uplink of TELSTAT := TRUE;
453  ;;@      END;
454  ;;
455           BSET     uplink_bsy,uplink_flags
456           CLI                              ;Enable interrupts
457           LDA      #HIGH lcap_marker       ;Get address MSB
458           STA      TELADHI                 ;Write to controller register
459  ;
460           LDA      #LOW lcap_marker        ;Get address LSB
461           STA      TELADLO                 ;Write to controller
462           LDA      #1                      ;Get byte count
463           STA      BYTCOUNT                ;Write to controller
464           LDA      #MARKER_ID              ;Get ID
465           STA      ULID                    ;Write to controller
466           BSET     RAM_uplink,TELSTAT      ;Start uplink
467           BRA      ULM_DONE                ;Thats all folks
468  ;
469  ;;@    ELSE
470  ;;@    BEGIN
471  ;;      (* If no markers are pending the flag one pending *)
472  ;;@       lcap_mrkr_pnd of uplink_flags := TRUE;
473  ;;@    END;
474  ;;
475  ;
476

Avocet 6805 Assembler v2.20, #01002   Chip=146805
========= R2 LSCAP INTERRUPT MODULE ============ File: LOC.ASM
=========  $Revision:  3.0  $ ============

477  ;ULM_LCP
478  ;
479           BSET     lcap_mrkr_pnd,uplink_flags
480                                             ;Jump if lcap marker pending
481  ;
482  ;;@    enable interrupts;
483  ;
484  ;ULM_DONE
485           CLI                              ;Enable interrupts
```

```
486 ;
487 ;  ----------------------------------------
488 ;
489    @       %ENDM
490    @
491    @       END;            (* UPLINK_LCAP_MARKER *)
492    @
493
494 $EJECT
495    Avocet 6805 Assembler v2.20, #0100?                              : ADC.ASM
       ========== R2 ADC INTERRUPT
       ========== $Revision: 3

187 ;**********************************************************************
188 ;*                    ADC Interrupt Macros                            *
189 ;**********************************************************************
190
191 ;@******************* UPLINK_MEAS_VAL ********************************
192 ;@*
193 ;@* This macro is used to uplink measured values.
194 ;@*
195 ;@* ENTRY CONDITIONS:
196 ;@*     The array meas_val has been loaded with the appropriate
197 ;@*     data for uplink. The number of bytes for uplink is stored
198 ;@*     in the x register.
199 ;@*
200 ;@* EXIT CONDITIONS:
201 ;@*     If the uplink channel is free it is captured and the data
202 ;@*     in the meas_val buffer is uplinked. If the uplink channel
203 ;@*     is busy with a RAM uplink the measured values are
204 ;@*     discarded. Otherwise if the channel is busy the measured
205 ;@*     values are flagged as pending and uplinked on the next
206 ;@*     TELBF interrupt.
207 ;@*
208 ;@*
209 ;@**********************************************************************
```

```
210 ;-------------------------------------------------
211 ;@   MACRO UPLINK_MEAS_VAL(x);
212 ;@   BEGIN
213 ;@     IF NOT(uplnk_disabled of uplink_flags) THEN
214 ;-------------------------------------------------
215 UPLINK_MEAS_VAL %MACRO
216 UMV_START
217           BRSET    uplnk_disabled,uplink_flags,UMV_END
218 ;-------------------------------------------------
219 ;@     BEGIN
220 ;@       IF NOT(uplink_bsy of uplink_flags) THEN
221 ;-------------------------------------------------
222                                          ;Jump if uplink busy
223           BRSET    uplink_bsy,uplink_flags,UMV_SMV
224 ;-------------------------------------------------
225 ;@       BEGIN
226 ;@       (* Uplink channel free uplink measured value buffer *)
227 ;@       uplink_bsy of uplink_flags := TRUE;
228 ;@       TELADHI := HIADDR(meas_val[0]);
229 ;@       TELADLO := LOADDR(meas_val[0]);
230 ;@       BYTCOUNT := x;
231 ;@       ULID := meas_id;
232 ;@       RAM_uplink of TELSTAT := TRUE;
233 ;@       END;
234 ;-------------------------------------------------
235           BSET     uplink_bsy,uplink_flags  ;Set uplink busy
236           LDA      #HIGH meas_val           ;Get buffer address MSB
237           STA      TELADHI                  ;Write DMA address register
238
239           LDA      #LOW meas_val            ;Get buffer address LSB
240           STA      TELADLO                  ;etc.
241           STX      BYTCOUNT                 ;Write byte count
242           LDA      meas_id                  ;Get ID
243           STA      ULID
244           BSET     RAM_uplink,TELSTAT       ;Write to hardware ;Start uplink
245           BRA      UMV_END                  ;Go exit
246 ;-------------------------------------------------
247 ;@     ELSE  (* NOT uplink_bsy *)
248 ;-------------------------------------------------
```

```
251  ;a          BEGIN
252  ;a            (* Set measured value uplink pending *)
253  ;a            meas_count := x;
254  ;a            meas_pnd of uplink_flags := TRUE;
255  ;a          END;
256  ;a        END;
257
258  ;---------------------------------------------------------------

Avocet 6805 Assembler v2.20, #01002   Chip=146805
       ========= R2 ADC INTERRUPT MODULE ============ File: ADC.ASM
       ========= $Revision:  3.0  $ =============

259  :UMV_SMV     STX     meas_count        ;Save pending byte count
260              BSET    meas_pnd,uplink_flags ;Show pending uplink
261              BRA     UMV_END           ;Thats all folks
262  :UMV_END     %ENDM
263
264
265
266  ;a   END;  (* UPLINK_MEAS_VAL *)
267  ;---------------------------------------------------------------
268
269  $EJECT Avocet 6805 Assembler v2.20, #01002   Chip=146805
       ========= R2 TELEMETRY MODULE ============ File: TLM.ASM
       ========= $Revision:  3.3  $ =============

378  ;a******************************************* TLM ******************************************
379  ;a*                                                                                        *
380  ;a*   R2, Pacemaker Model 8444                                                             *
381  ;a*   MODULE:    TLM                                                                       *
382  ;a*                                                                                        *
383  ;a*   The TLM module processes magnet mode operations while the reed                       *
384  ;a*   switch is closed. These include the handling of the telemetry                        *
385  ;a*   protocol, the TMT and lead test activation, the pulse pressure                       *
386  ;a*   calculation for loss of capture markers detection. The                               *
387  ;a*   telemetry protocol involves processing downlink and uplink                           *
388  ;a*   messages. Downlink messages are validated before being acted                         *
389  ;a*   upon. The uplink consists of confirmation and confirmation +                         *
390  ;a*   replies to downlink requests.                                                        *
391  ;a*                                                                                        *
```

```
392 ;@*   Routines defined in this module include:
393 ;@*
394 ;@*   Macros:
395 ;@*       DO_MEMWRITE            - transfer downlink record to
396 ;@*                                memory
397 ;@*       EXEC_SPEC_FUNC         - decode and execute special
398 ;@*                                function
399 ;@*       EXEC_SPEC_REQ          - decode and execute special
400 ;@*                                requests
401 ;@*       PROCESS_MEMWRITE       - transfer downlink record to
402 ;@*                                memory     and evaluate it
403 ;@*       PROCESS_MSG            - decode memory offsets
404 ;@*       SWITCH_TO_NON_MAGMODE  - restore non_magnet mode
405 ;@*                                operation
406 ;@*       VALIDATE_MSG           - validate downlink message
407 ;@*
408 ;@*   Procedures:
409 ;@*       None.
410 ;@*
411 ;@*   Drivers:
412 ;@*       GNLSINT_PROC           - gain or loss interrupt handler
413 ;@*       RDSWINT_PROC           - reed-switch interrupt handler
414 ;@*       TELBFINT_PROC          - telemetry buffer interrupt
415 ;@*                                handler
416 ;@*
417 ;@***************************************************************
418
419
420             DEFSEG    TLM,CLASS=CODE
421             SEG       TLM
422
423  $SETLN(MACROS.INC);         %INCLUDE "MACROS.INC"

Avocet 6805 Assembler v2.20, #01002   Chip=146805
     =========== R2 TELEMETRY MODULE ================= File: TLM.ASM
     =========== $Revision: 3.3 $ =============

424  $NOALLPUBLIC
425
426  $SETLN(EQUATES.INC);        %INCLUDE "EQUATES.INC"
```

```
Avocet 6805 Assembler v2.20, #01002  Chip=146805
========= R2 TELEMETRY MODULE ================== File: TLM.ASM
=========  $Revision:   3.3  $  =============
```

```
;********************************************************************
;*                                                                  *
;*                    Telemetry Subroutines                         *
;*                                                                  *
;********************************************************************
$EJECT
;********************************************************************
;*                  Telemetry Interrupt Handlers                    *
;********************************************************************
;a************************ GNSLINT_PROC *****************************
;a*                                                                 *
;a*  This procedure is the gain/loss interrupt handler and it is    *
;a*  non-preemptive. It is responsible for controlling the downlink *
;a*  and disabling uplink. Whether the interrupt is do to a gain or a *
;a*  loss of signal can be determined by reading a bit in the TELSTAT *
;a*  register. At the beginning of a downlink all pending uplinks are *
;a*  abandoned and the TELBF interrupt is masked out until the end of *
;a*  downlink. In which case it is reenabled, after being first      *
;a*  cleared, in the case of downlink overrun. Downlink is then     *
;a*  disabled until just before the uplink response, either a status *
;a*  uplink or a RAM uplink.                                        *
;a*                                                                 *
;a*  ENTRY CONDITIONS:                                              *
;a*     No other interrupts are enabled at this point, ADC interrupts *
;a*     are the only higher priority and they are ignored during    *
;a*     telemetry.                                                  *
;a*                                                                 *
;a*  EXIT CONDITIONS:                                               *
;a*     None.                                                       *
;a*                                                                 *
;a************************************************************************
```

```
1843  ;@PROCEDURE GNLSINT_PROC;
1844  ;@BEGIN
1845  ;@
1846  ;@  (* Check if gain or loss of signal occurred. *)
1847  ;@  IF (downlnk_present of TELSTAT) THEN
1848  ;@  BEGIN
1849  ;@    (* Gain of downlink signal. Clear pending uplinks, disable
1850  ;@        uplink and TELBF interrupts, and clear any ADC and           *)
1851  ;@        TELBFINT interrupts.
1852  ;@    uplink_flags := UPLNK_GN_SET;
1853  ;@    IF (TMT of mag_flags) THEN
1854  ;@      reset_TMT of mag_flags := TRUE;
1855  ;@    TELBFINT of ipgstate_msk := TRUE;
1856  ;@    IRQREG := TELBFINT_MSK;
1857  ;@    ULID := 0;
1858  ;@
1859  ;@  (* If POS currently executing then postpone loss-of-signal
1860  ;@      processing until after POS is complete.                         *)
1861  ;@  IF ((sensed_evnt of exec_flags)
1862  ;@      OR (paced_evnt of exec_flags)) THEN
1863  ;@    GNLSINT of current_pri := TRUE;
1864  ;@  END;
1865  ;@
1866  ;@
1867  ;@
1868  GNLSINT_PROC
1869                BRCLR    downlnk_present,TELSTAT,GNLS_LOSS
1870                LDA      #UPLNK_GN_SET
1871                STA      uplink_flags         ;Disable uplink
1872                BRCLR    TMT,mag_flags,GNLS_NTMT
1873                BSET     reset_TMT,mag_flags  ;Reset TMT if active
1874  GNLS_NTMT
1875                BSET     TELBFINT,ipgstate_msk  ;Mask TELBF interrupts
1876                LDX      #TELBFINT_MSK
1877                STX      IRQREG                 ;Clear TELBF interrupts
1878                CLRA
1879                STA      ULID                   ;Clear ULID register
1880                LDA      exec_flags             ;Is POS currently executing?
1881                AND      #((1 SHL sensed_evnt) + (1 SHL paced_evnt))
1882                BEQ      GNLS_NPOS              ; No, then exit
1883                BSET     GNLSINT,current_pri    ; Yes, postpone loss-o-signal
1884                                                ;   until after POS

0000&  09 00* 1D
0003&  A6 03
0005&  B7 00*
0007&  09 00* 02
000A&  1A 00*

000C&  14 00*
000E&  AE 04
0010&  BF 00*
0012&  4F
0013&  B7 00*
0015&  B6 00*
0017&  A4 03
0019&  27 02
001B&  12 00*
```

```
Avocet 6805 Assembler v2.20, #01002   Chip=146805
========== R2 TELEMETRY MODULE ================= File: TLM.ASM
========== $Revision: 3.3 $ =============

1885   GNLS_NPOS
001D& CC 0384&            1886            JMP      GNLS_DONE
                          1887   ;------------------------------------------
                          1888   ;@ ELSE IF (uplnk_disabled of uplink_flags) THEN
                          1889   ;@ BEGIN
                          1890   ;@   (* If the uplnk_disabled bit was not set then a downlink
                          1891   ;@      overrun has occured (gain of signal was missed) and
                          1892   ;@      downlink should be ignored!!                        *)
                          1893   ;@
                          1894   ;@   IF (reset_TMT of mag_flags) THEN
                          1895   ;@     CALL TMT_RESET WITHIN R2LIB;
                          1896   ;@
                          1897   ;@   uplnk_stat := (uplnk_stat AND UPLNK_CLR_MSK);
                          1898   ;@
                          1899   ;@   IF (TELBFINT of IRQREG) THEN
                          1900   ;@   BEGIN
                          1901   ;@     (* Downlink overflow - Flag error, uplink status,
                          1902   ;@        and clear TELBF interrupt *)
                          1903   ;@     IRQREG := TELBFINT_MSK;
                          1904   ;@     up_stat_pnd of uplink_flags := TRUE;
                          1905   ;@     uplnk_stat := uplnk_stat OR DNLK_OVF_ERR;
                          1906   ;@   END;
                          1907   ;------------------------------------------
                          1908   GNLS_LOSS
0020& 00 00* 03           1909            BRSET    uplnk_disabled,uplink_flags,GNLS_LCONT
0023& CC 0384&            1910            JMP      GNLS_DONE
                          1911   GNLS_LCONT
0026& 0B 00* 03           1912            BRCLR    reset_TMT,mag_flags,GNLS_NTMTRST
0029& CD 0000*            1913            JSR      TMT_RESET     ;Go abort TMT sequence
```

```
                GNLS_NTMTRST
002C& B6 00*                  LDA     uplnk_stat
002E& A4 F0                   AND     #UPLNK_CLR_MSK
0030& B7 00*                  STA     uplnk_stat        ;Mask error bits in uplink status
0032& 05 00* 0D               BRCLR   TELBFINT,IRQREG,GNLS_NOVF   ;Has downlink overflow occurred?
0035& AE 04                   LDX     #TELBFINT_MSK
0037& BF 00*                  STX     IRQREG                      ;Clear TELBF interrupts
0039& 16 00*                  BSET    up_stat_pnd,uplink_flags    ;Set status uplink pending
003B& AA 09                   ORA     #DNLK_OVF_ERR
003D& B7 00*                  STA     uplnk_stat                  ;Set and store Overflow error
003F& CC 0350&                JMP     GNLS_UPLNK 1925    ;@
1926    ;@      ELSE
1927    ;@      BEGIN
1928    ;@        (* No downlink overflow *)
1929    ;@        CALLM VALIDATE_MSG;
1930    ;@      END;
1931    ;@
1932    ;@------------------------------------------------------------------
                GNLS_NOVF         ;VALIDATE_MSG
1934    ;@------------------------------------------------------------------
1935    ;@   (* Request event time to be latched (write any value)
1936    ;@      NOTE: event time takes 0.244msec to be latched *)
1937    ;@   EVENTIME := 0;
1938    ;@
1939    ;@   IF ((up_RAM_pnd of uplink_flags)
1940    ;@       OR (intrrg_pnd of uplink_flags)) THEN
1941    ;@   BEGIN
1942    ;@     (* Only allow RAM uplink if the pacing interval is above
1943    ;@        HIGH_RATE, otherwise clear uplink status flag.           *)
1944    ;@     IF (timeout_int < HIGH_RATE) THEN
1945    ;@     BEGIN
1946    ;@       up_RAM_pnd of uplink_flags := FALSE;
1947    ;@       intrrg_pnd of uplink_flags := FALSE;
1948    ;@       up_stat_pnd of uplink_flags := TRUE;
1949    ;@     END;
1950    ;@     ELSE
1951    ;@       up_stat_pnd of uplink_flags := FALSE;
1952    ;@   END;
```

```
Avocet 6805 Assembler v2.20, #01002   Chip=146805
========== R2 TELEMETRY MODULE ================= File: TLM.ASM
========== $Revision: 3.3 $ ==============

1953   ;-------------------------------------------------------------------
                    1954   GNLS_UPLNK
                    1955
                    1956   GNLS_UPEVNT       STA     EVENTIME         ;Latch event time count
0350& B7 00*        1957                     LDA     uplink_flags
0352& B6 00*        1958                     AND     #((1 SHL up_RAM_prd) + (1 SHL intrrg_prd))
0354& A4 14         1959                     BEQ     GNLS_NRAMUP      ;Jump if no RAM of interrogate uplink
0356& 27 11         1960                     LDA     timeout_int
0358& C6 0000*      1961                     CMP     #HIGH_RATE       ;Is timeout less then upper rate limit?
035B& A1 23         1962                     BHS     GNLS_RTLO        ; No, set uplink status flag false
035D& 24 08         1963                     BCLR    up_RAM_prd,uplink_flags
035F& 15 00*        1964                     BCLR    intrrg_prd,uplink_flags
0361& 19 00*        1965                     BSET    up_stat_prd,uplink_flags
0363& 16 00*        1966                     BRA     GNLS_NRAMUP
0365& 20 02         1967   GNLS_RTLO
                    1968   GNLS_NRAMUP       BCLR    up_stat_prd,uplink_flags
0367& 17 00*        1969   ;-------------------------------------------------------------------
                    1970        (* If IPG in VVT mode switch to VVI mode until next event
                    1971            and sceduule uplink if there is enough time.            *)
                    1972        triggered_mode of PACEMODE := FALSE;
                    1973   ;@   a := timeout_int - EVENTIME
                    1974   ;@   IF (((a > UPSTAT_DELAY) AND (up_stat_prd of uplink_flags))
                    1975   ;@       OR (a > UPLINK_DELAY)) THEN
                    1976   ;@       CALL SCHEDULE_UPLINK WITHIN R2LIB;
                    1977   ;@   ELSE
                    1978   ;@       uplnk_cnfrm of tlm2_flags := TRUE;
                    1979
                    1980
```

```
0369& 15 00*                        BCLR    triggered_mode,PACEMODE   ;Set in non-VVT mode
036B& C6 0000*                      LDA     timeout_int
036E& B0 00*                        SUB     EVENTIME                  ;Determine time remaining before next event
0370& A1 1E                         CMP     #UPLINK_DELAY             ;Enough time for block uplink?
0372& 22 07                         BHI     GNLS_SU                   ; Yes, then schedule uplink
0374& 07 00* 09                     BRCLR   up_stat_pnd,uplink_flags,GNLS_NUPLNK
0377& A1 03                         CMP     #UPSTAT_DELAY             ;Enough time for status uplink?
0379& 23 05                         BLS     GNLS_NUPLNK               ; No, don't attempt uplink
                        ;
                        GNLS_SU
037B& CD 0000*                      JSR     SCHEDULE_UPLINK
037E& 20 02                         BRA     GNLS_CTLBF
                        ;
                        GNLS_NUPLNK
0380& 18 00*                        BSET    uplnk_cnfrm,tlm2_flags    ;Indicate uplink to follow next event
                        ;@     (* Enable TELBF interrupts and clear ADC interrupts *)
                        ;@     TELBFINT of ipgstate_msk := FALSE;
                        ;@     END;
                        ;@     IRQREG := ADCINT_MSK;
                        GNLS_CTLBF
0382& 15 00*                        BCLR    TELBFINT,ipgstate_msk
                        GNLS_DONE
0384& A6 01                         LDA     #ADCINT_MSK
0386& B7 00*                        STA     IRQREG                    ;Clear pending ADC interrupts
                        GNLS_END
0388& 81                            RTS
                        ;------------------------------------------------------------
                        ;@END;      (* GNLSINT_PROC *)
                        ;------------------------------------------------------------
                        $EJECT
```

Avocet 6805 Assembler v2.20, #01002   Chip=146805
========== R2 TELEMETRY MODULE ================= File: TLM.ASM
========== $Revision: 3.3 $ =============

```
2071     ;@********************** TELBFINT_PROC ***********************
2072     ;@*                                                          *
2073     ;@* This procedure is the telemetry buffer interrupt handler. It is *
2074     ;@* non-preemptive. It is responsible for scheduling pending uplinks *
2075     ;@* (i.e. markers). If the last uplink was a RAM uplink, all pending *
2076     ;@* uplinks are cancelled. Otherwise, if there is a pending   *
2077     ;@* interrogate block or measured value, they are uplinked.   *
2078     ;@*                                                          *
2079     ;@* ENTRY CONDITIONS:                                         *
2080     ;@*   No other interrupts are allowed during this routine, ADC must *
2081     ;@*   be cleared if one occurred during uplink reschedule, and *
2082     ;@*   processing of GAIN/LOSS must wait until after uplink TELBF *
2083     ;@*   completes to insure that the uplink flags are not corrupted *
2084     ;@*                                                          *
2085     ;@* EXIT CONDITIONS:                                          *
2086     ;@*   None.                                                   *
2087     ;@*                                                          *
2088     ;@************************************************************
2089     ;
2090     ;@PROCEDURE TELBFINT_PROC;
2091     ;@BEGIN
2092     ;@
2093     ;@ (* If RAM uplink complete clear all pending uplinks *)
2094     ;@ IF (uplnk_disabled of uplink_flags) THEN
2095     ;@   uplink_flags := 0;
2096     ;@
2097     ;-----------------------------------------------------------
2098     TELBFINT_PROC
2099                    BRCLR    uplnk_disabled,uplink_flags,TLBF_UPLNK
04238 01 00* 05
04268 4F      2100     CLRA
04278 B7 00*  2101     STA      uplink_flags   ;Clear all pending uplink
04298 20 68   2102     BRA      TLBF_DONE
               2103     ;
```

```
2104  ;@    ELSE
2105  ;@    BEGIN
2106  ;@      (* Previous uplink was not a RAM uplink, uplink pending *)
2107  ;@      IF (mrkr_pnd of uplink_flags) THEN
2108  ;@      BEGIN
2109  ;@        (* Marker from POS is pending *)
2110  ;@        mrkr_pnd of uplink_flags := FALSE;
2111  ;@        TELADHI := HIADDR(marker_val[0]);
2112  ;@        TELADLO := LOADDR(marker_val[0]);
2113  ;@        BYTCOUNT := marker_cnt;
2114  ;@        ULID := MARKER_ID;
2115  ;@        RAM_uplink of TELSTAT := TRUE;
2116  ;@      END;
2117  ;@
2118  ;@;-------------------------------------------------------------------
2119         TLBF_UPLNK
2120  042B& 0D 00* 11          BRCLR    mrkr_pnd,uplink_flags,TLBF_LCAP
2121  042E& 1D 00*              BCLR     mrkr_pnd,uplink_flags
2122  0430& A6 ..X              LDA      #HIGH marker_val        ;Load register with hi address of marker value
                                                                ;                                      address
2123  0432& B7 00*              STA      TELADHI
2124  0434& A6 ..X              LDA      #LOW marker_val         ;Load register with low address of marker value
                                                                ;                                      address
2125  0436& B7 00*              STA      TELADLO
2126  0438& CE 0000*            LDX      marker_cnt              ;Load x with byte count
2127  043B& A6 43               LDA      #MARKER_ID              ;Load a with marker identification byte
2128  043D& 20 49               BRA      TLBF_STRTU
2129  ;@;-------------------------------------------------------------------
2130  ;@    ELSE IF (lcap_mrkr_pnd of uplink_flags) THEN
2131  ;@    BEGIN
2132  ;@      (* Marker from loss of capture is pending *)
2133  ;@      lcap_mrkr_pnd of uplink_flags := FALSE;
2134  ;@      TELADHI := HIADDR(lcap_marker);
2135  ;@      TELADLO := LOADDR(lcap_marker);
2136  ;@      BYTCOUNT := 1;
```

```
Avocet 6805 Assembler v2.20, #01002   Chip=146805
========== R2 TELEMETRY MODULE ====================== File: TLM.ASM
========== $Revision: 3.3  $ ==============

2137         ;@       ULID := MARKER_ID;
                    2138         ;@       RAM_uplink of TELSTAT := TRUE;
                    2139         ;@     END;
                    2140         ;@
                    2141         ;------------------------------------------------------
                    2142         TLBF_LCAP
043F& 0B 00* 10     2143              BRCLR    lcap_mrkr_pnd,uplink_flags,TLBF_INTRRG
0442& 1B 00*        2144              BCLR     lcap_mrkr_pnd,uplink_flags
0444& A6 ..X        2145              LDA      #HIGH lcap_marker   ;Load register with hi address of lcap marker v
                                                                    alue address
0446& B7 00*        2146              STA      TELADHI
0448& A6 ..X        2147              LDA      #LOW lcap_marker    ;Load register with low address byte of lcap ma
                                                                    rker value address
044A& B7 00*        2148              STA      TELADLO
044C& AE 01         2149              LDX      #1                  ;Load x with byte count
044E& A6 43         2150              LDA      #MARKER_ID          ;Load a with marker identification byte
0450& 20 36         2151              BRA      TLBF_STRTU
                    2152         ;@     ELSE IF (intrrg_pnd of uplink_flags) THEN
                    2153         ;@       BEGIN
                    2154         ;@         intrrg_pnd of uplink_flags := FALSE;
                    2155         ;@         statbyt := uplnk_stat;
                    2156         ;@         CALLM LOAD_INTRRG_UPLINK WITHIN R2LIB;
                    2157         ;@         RAM_uplink of TELSTAT := TRUE;
                    2158         ;@       END;
                    2159         ;@
                    2160         ;------------------------------------------------------
                    2161         TLBF_INTRRG
0452& 09 00* 20     2162              BRCLR    intrrg_pnd,uplink_flags,TLBF_MEAS
0455& 19 00*        2163              BCLR     intrrg_pnd,uplink_flags
0457& B6 00*        2164              LDA      uplnk_stat
0459& C7 0000*      2165              STA      statbyt             ;Update status byte
```

```
                    TLBF_LDIN       ;LOAD_INTRRG_UPLINK
0471& 16 00*                        BSET    RAM_uplink,TELSTAT      ;Initiate uplink
0473& 20 1E                         BRA     TLBF_DONE
                    TLBF_LDIN_END
                    ;-----------------------------------------------------------
                    ;@      ELSE IF (meas_pnd of uplink_flags) THEN
                    ;@      BEGIN
                    ;@          meas_pnd of uplink_flags := FALSE;
                    ;@          TELADHI := HIADDR(meas_val[0]);
                    ;@          TELADLO := LOADDR(meas_val[0]);
                    ;@          BYTCOUNT := meas_count;
                    ;@          ULID := meas_id;
                    ;@          RAM_uplink of TELSTAT := TRUE;
                    ;@      END;
                    ;-----------------------------------------------------------
                    TLBF_MEAS
0475& 0F 00* 18                     BRCLR   meas_pnd,uplink_flags,TLBF_NUPLNK
0478& 1F 00*                        BCLR    meas_pnd,uplink_flags
047A& A6 ..X                        LDA     #HIGH meas_val          ;Load register with hi address of measured valu
                                                                     e address
047C& B7 00*                        STA     TELADHI
047E& A6 ..X                        LDA     #LOW meas_val           ;Load register with low address byte of measure
                                                                     d value address
0480& B7 00*                        STA     TELADLO
0482& CE 0000*                      LDX     meas_count              ;Load x with byte count
0485& C6 0000*                      LDA     meas_id                 ;Load a with marker identification byte
                    TLBF_STRTU
0488& BF 00*                        STX     BYTCOUNT                ;Store byte count
048A& B7 00*                        STA     ULID                    ;Store marker identification byte
048C& 16 00*                        BSET    RAM_uplink,TELSTAT      ;Set the telemetry status byte and exit
048E& 20 03                         BRA     TLBF_DONE
                    ;-----------------------------------------------------------
                    ;@      ELSE (* No pending uplinks *)
                    ;@          uplink_flags := 0;
                    ;@      END;
                    ;@      (* Clear pending ADC interrupts *)
```

```
Avocet 6805 Assembler v2.20, #01002  Chip=146805
========= R2 TELEMETRY MODULE ================== File:
========= $Revision: 3.3 $ =============

2201            ;@ IRQREG := ADCINT_MSK;
2202            ;@
2203            ;------------------------------------------------------------
2204   TLBF_NUPLNK
2205              CLRA
2206              STA      uplink_flags    ;Clear uplink flags, no uplinks pending
2207   TLBF_DONE
2208              LDA      #ADCINT_MSK
2209              STA      IRQREG          ;Clear pending ADC interrupts
2210   TLBF_END
2211              RTS
2212            ;------------------------------------------------------------
2213            ;@END;  (* TELBFINT_PROC.*)
2214            ;@
2215            ;------------------------------------------------------------
2216              END
```

```
04908 4F
04918 B7 00*

04938 A6 01
04958 B7 00*

04978 81
```

```
Avocet 6805 Assembler v2.20, #01002  Chip=146805
========= R2 LIBRARY MODULE ================== File: R2LIB.ASM
========= $Revision: 3.3 $ =============

120  ;@***************** LOAD_INTRRG_UPLINK ********************************
121  ;@*                                                                   *
122  ;@*  This macro loads the telemetry registers in preparation for an   *
123  ;@*  Interrogate block uplink.                                        *
124  ;@*                                                                   *
125  ;@*  ENTRY CONDITIONS:                                                *
126  ;@*    Uplink data registers are ready to be loaded without conflict. *
127  ;@*                                                                   *
128  ;@*  EXIT CONDITIONS:                                                 *
129  ;@*    The interrogate block the size of INTRRG_SIZ and starting at   *
130  ;@*    the address pointed to by INTRRG_AD is setup for uplink.       *
131  ;@*                                                                   *
132  ;@*                                                                   *
133  ;@********************************************************************
```

```
;------------------------------------------------------------
;@    MACRO LOAD_INTRRG_UPLINK;
;@    BEGIN
;@
;@        (* Load interrogate status byte *)
;@        intrrg_R2_stat := R2_stat;
;@        (* Uplink channel assumed free and uplnk_disabled bit set *)
;@        TELADHI := HIBYTE(INTRRG_AD);
;@        TELADLO := LOWBYTE(INTRRG_AD);
;@        BYTCOUNT := INTRRG_SIZ;
;@        ULID := RAM_ID;
;@
;@    END;      (* LOAD_INTRRG_UPLINK *)
;------------------------------------------------------------
LOAD_INTRRG_UPLINK %MACRO
        LDA     r2_stat             ;Get r2 status byte
        STA     intrrg_r2_stat      ;put in interrogate status byte
        LDA     #HIGH_INTRRG_AD     ;Get address hi byte
        STA     TELADHI             ;Send it to the hardware LDA     #LOW_INTRRG_AD      ;Get address lo byte
        STA     TELADLO             ;Send it to the hardware LDA     #INTRRG_SIZ         ;Get byte count
        STA     BYTCOUNT            ;Write hardware register
        LDA     #RAM_ID             ;Get ID
        STA     ULID                ; etc. etc. etc.
        %ENDM $EJECT
Avocet 6805 Assembler v2.20, #01002    Chip=146805
============ R2 LIBRARY MODULE ================= File: R2LIB.ASM
============ $Revision:    3.3    $ =============
```

;@********************** LOAD_RAM_UPLINK ***************************
;@*                                                                    *
;@*  This macro loads the telemetry registers in preparation for a     *
;@*  RAM block uplink.                                                 *

```
169  ;@*   ENTRY CONDITIONS:                                                      *
170  ;@*     Uplink data registers are ready to be loaded without conflict.       *
171  ;@*                                                                          *
172  ;@*   EXIT CONDITIONS:                                                       *
173  ;@*     A RAM block of length indicated by P_rd_bytes starting at the        *
174  ;@*     address indicated by P_rd_start is setup for uplink.                 *
175  ;@*                                                                          *
176  ;@****************************************************************************
177
178  ;@   MACRO LOAD_RAM_UPLINK;
179  ;@   BEGIN
180  ;@
181  ;@     (* Uplink channel assumed free and uplnk_disabled bit set *)
182  ;@     intrrg_R2_stat := R2_stat;
183  ;@     TELADHI := HIBYTE(P_rd_start);
184  ;@     TELADLO := LOWBYTE(P_rd_start);
185  ;@     BYTCOUNT := P_rd_bytes;
186  ;@     ULID := RAM_ID;
187  ;@
188  ;@   END;    (* LOAD_RAM_UPLINK *)
189
190  ;-----------------------------------------------------------------------------
191  LOAD_RAM_UPLINK %MACRO
192          LDA     r2_stat         ;Get r2 status byte
193          STA     intrrg_r2_stat  ;put in interrogate status byte
194          LDA     P_rd_start      ;Get address hi byte
195          STA     TELADHI         ;Send it to the hardware
196
197          LDA     P_rd_start +1   ;Get address lo byte
198          STA     TELADLO         ;Send it to the hardware
199
200          LDA     P_rd_bytes      ;Get byte count
201          STA     BYTCOUNT        ;Write hardware register
202          LDA     #RAM_ID         ;Get ID
203          STA     ULID            ; etc. etc. etc.
204          %ENDM
205
206
```

```
207        $RESETLN
239
240        $NOALLPUBLIC
241        $NOLIST                          ;Don't List the equate file Avocet 6805 Assembler v2.20, #01002   Chip=146805
           ========= R2 LIBRARY MODULE ================== File: R2LIB.ASM
           =========  $Revision:   3.3    $ ==============

1106  ;@************************ SCHEDULE_UPLINK ***************************
1107  ;@*                                                                   *
1108  ;@*   This procedure schedules uplink of RAM, interrogate block, or   *
1109  ;@*   status in this order of priority.                               *
1110  ;@*                                                                   *
1111  ;@* ENTRY CONDITIONS:                                                  *
1112  ;@*   No other interrupts are allowed during this routine, ADC        *
1113  ;@*   interrupts must be cleared if one occurred during uplink        *
1114  ;@*   scheduling. Processing of the GAIN/LOSS and TLBF interrupts     *
1115  ;@*   wait until after uplink is scheduled to ensure that the         *
1116  ;@*   uplink flags are not corrupted.                                 *
1117  ;@*                                                                   *
1118  ;@* EXIT CONDITIONS:                                                   *
1119  ;@*   Either a RAM block, an Interrogate block, or a status           *
1120  ;@*   confirmation block are uplinked if any are pending.             *
1121  ;@*   Status is imbedded in a RAM or Interrogate block uplink.        *
1122  ;@*                                                                   *
1123  ;@*********************************************************************
1124  ;------------------------------------------------------------
1125  ;@  PROCEDURE SCHEDULE_UPLINK;
1126  ;@  BEGIN
1127  ;@
1128  ;@     (* Load status byte for RAM uplink and the load telemetry
1129  ;@        registers for uplink. *)
1130  ;@     IF (up_RAM_pnd of uplink_flags) THEN
1131  ;@        BEGIN
1132  ;@            (* Load for Ram uplink *)
1133  ;@            CALLM LOAD_RAM_UPLINK;
1134  ;@            up_RAM_pnd of uplink_flags := FALSE;
1135  ;@        END;
1136  ;@
```

```
                    ;-------------------------------------------------------------
                    SCHEDULE_UPLINK
                    ;-------------------------------------------------------------
0180& 05 00* 1D         BRCLR   up_RAM_pnd,uplink_flags,SUP_INTRRG  ;Jump if NOT RAM uplink
                    SU_LRU
                            ;LOAD_RAM_UPLINK
0183& B6 00*                LDA     r2_stat             ;Get r2 status byte
0185& C7 0000*              STA     intrrg_r2_stat      ;put in interrogate status byte
0188& C6 0000*              LDA     P_rd_start          ;Get address hi byte
018b& B7 00*                STA     TELADHI             ;Send it to the hardware 018D& C6 ....X              LDA     P_rd_start +1       ;Get address lo byte
0190& B7 00*                STA     TELADLO             ;Send it to the hardware 0192& C6 0000*              LDA     P_rd_bytes          ;Get byte count
0195& B7 00*                STA     BYTCOUNT            ;Write hardware register
0197& A6 C0                 LDA     #RAM_ID             ;Get ID
0199& B7 00*                STA     ULID                ; etc. etc. etc.

SU_LRU_END
019B& 15 00*                BCLR    up_RAM_pnd,uplink_flags  ;Clear the pending flag
019D& CC 01D1&              JMP     SUP_STRT                 ;Go start uplink
                    ;-------------------------------------------------------------
                    ;@  ELSE IF (intrrg_pnd of uplink_flags) THEN
                    ;@     BEGIN
                    ;@        (* Load for interrogate block uplink *)
                    ;@        CALLM LOAD_INTRRG_UPLINK WITHIN R2LIB;
                    ;@        intrrg_pnd of uplink_flags := FALSE;
                    ;@     END;
                    ;-------------------------------------------------------------
                    SUP_INTRRG
01A0& 09 00* 1A         BRCLR   intrrg_pnd,uplink_flags,SUP_STAT  ;Jump if NOT interrogate
                    SU_LIU
                            ;LOAD_INTRRG_UPLINK
01A3& B6 00*                LDA     r2_stat             ;Get r2 status byte
01A5& C7 0000*              STA     intrrg_r2_stat      ;put in interrogate status byte
```

```
Avocet 6805 Assembler v2.20, #01002    Chip=146805
========== R2 LIBRARY MODULE ==================== File: R2LIB.ASM
========== $Revision:   3.3    $ ==============

01A8&  A6 ..X         1174              LDA    #HIGH INTRRG_AD  ;Get address hi byte
01AA&  B7 00*         1175              STA    TELADHI          ;Send it to the hardware
                      1176
01A8&  A6 ..X         1177              LDA    #LOW INTRRG_AD   ;Get address lo byte
01AA&  B7 00*         1178              STA    TELADLO          ;Send it to the hardware
                      1179
01B0&  A6 00*         1180              LDA    #INTRRG_SIZ      ;Get byte count
01B2&  B7 00*         1181              STA    BYTCOUNT         ;Write hardware register
01B4&  A6 C0          1182              LDA    #RAM_ID          ;Get ID
01B6&  B7 00*         1183              STA    ULID             ; etc. etc. etc.
                      1184   SU_LIU_END
01B8&  19 00*         1185              BCLR   intrrg_pnd,uplink_flags  ;Clear the flag
01BA&  CC 01D1&       1186              JMP    SUP_STRT                 ;Go start uplink
                      1187
                      1188   ;------------------------------------------
                      1189   ;@     ELSE IF (up_stat_pnd of uplink_flags) THEN
                      1190   ;@     BEGIN
                      1191   ;@        (* Load for status ID byte for uplink *)
                      1192   ;@        ULID := STATUS_ID;
                      1193   ;@        up_stat_pnd of uplink_flags := FALSE;
                      1194   ;@     END;
                      1195   ;------------------------------------------
                      1196   SUP_STAT
                      1197
01BD&  07 00* 08      1198              BRCLR  up_stat_pnd,uplink_flags,SUP_NO_UP  ;Jump if NOT status ID byte
01C0&  A6 80          1199              LDA    #STATUS_ID
01C2&  B7 00*         1200              STA    ULID                               ;Write status ID to hardware
01C4&  17 00*         1201              BCLR   up_stat_pnd,uplink_flags           ;Clear the flag
01C6&  20 09          1202              BRA    SUP_STRT                           ;Go start Uplink
                      1203

Avocet 6805 Assembler v2.20, #01002    Chip=146805
========== R2 LIBRARY MODULE ==================== File: R2LIB.ASM
========== $Revision:   3.3    $ ==============
```

```
1204         ;@      ELSE
1205         ;@      BEGIN
1206         ;@        (* No uplink scheduled reset telemetry and exit routine *)
1207         ;@        uplink_flags := 0;
1208         ;@        CALL SET_TLM_TYPE
1209         ;@        downlink_enable of TELSTAT := TRUE;
1210         ;@        EXIT;
1211         ;@      END;
1212         ;
1213         ;-----------------------------------------------------------------
1214         SUP_NO_UP
01C8& 3F 00*   1215           CLR       uplink_flags       ;Clear uplink_flags, no uplink
01CA& CD 01DE& 1216           JSR       SET_TLM_TYPE       ;Set telemetry type and enable downlink
01CD& 1A 00*   1217           BSET      downlink_enabled,TELSTAT
01CF& 20 0C    1218           BRA       SUP_END            ;Go exit
1219         ;-----------------------------------------------------------------
1220         ;@      (* Set telemetry type start uplink and enable downlink *)
1221         ;@      statbyt := uplink_stat;
1222         ;@      CALL SET_TLM_TYPE;
1223         ;@      downlink_enable of TELSTAT := TRUE;
1224         ;@      RAM_uplink of TELSTAT := TRUE;
1225         ;
1226         ;
1227         ;-----------------------------------------------------------------
1228         SUP_STRT
01D1& B6 00*   1229           LDA       uplink_stat        ;Get uplink status
01D3& C7 0000* 1230           STA       statbyt
01D6& CD 01DE& 1231           JSR       SET_TLM_TYPE       ;Set telemetry type
01D9& AA 28    1232           ORA       #(1 SHL RAM_uplink) + (1 SHL downlink_enabled)
01DB& B7 00*   1233           STA       TELSTAT            ;enable downlink and start uplink
1234         SUP_END
01DD& 81       1235           RTS                          ;Return to caller
1236         ;-----------------------------------------------------------------
1237         ;@      END; (* SCHEDULE_UPLINK *)
1238         ;-----------------------------------------------------------------
1239         
1240         $EJECT
1241         ;@****************** SET_TLM_TYPE ******************************
1242         ;@*                                                            *
```

```
1243  ;@* ****************************************************
1244  ;@* This procedure decodes the telemetry type in P_tlm_type and
1245  ;@* sets up the hardware and marker channel accordingly.
1246  ;@*
1247  ;@* ENTRY COND. :
1248  ;@*   P_tlm_type contains the desired telemetry.
1249  ;@*
1250  ;@* EXIT COND. :
1251  ;@*   The analog uplink telemetry is updated on the next frame.
1252  ;@*   Curr_tlm_type is written to PACESTAT and may not equal
1253  ;@*   P_tlm_type.
1254  ;@*   a - contains the current value of the TELSTAT register.
1255  ;@*****************************************************
1256
1257  ;@ PROCEDURE SET_TLM_TYPE;
1258  ;@ BEGIN
1259  ;@
1260  ;@   (* test for markers uplink selected *)
1261  ;@   IF (marker_enabled of P_tlm_type := TRUE) THEN
1262  ;@     marker_active of mag_flags := TRUE;
1263  ;@   ELSE
1264  ;@     marker_active of mag_flags := FALSE;
1265  ;@
1266
1267  SET_TLM_TYPE   LDA   P_tlm_type        ;Jump if idle markers set
1268                 AND   #(1 SHL marker_enabled)
1269                 BEQ   STT_ICLR
1270                 BSET  markers_active,mag_flags  ;Show idle markers
1271                 BRA   STT_ADJ           ;Go adjust telem type
1272
1273  STT_ICLR       BCLR  markers_active,mag_flags
1274
1275  ;@   (* adjust the telemetry type *)
1276  ;@   curr_tlm_type := (P_tlm_type AND TLM_TYPE_MSK) OR IDLE_UPLINK;
1277  ;@   TELSTAT := (TELSTAT AND TELSTAT_MSK) OR curr_tlm_type;
1278  ;@
```

01DE& C6 0000*
01E1& A4 01
01E3& 27 04
01E5& 1E 00*
01E7& 20 02

01E9& 1F 00*

```
01EB& C6 0000*    1283  STT_ADJ   LDA   p_tlm_type         ;Get telemetry type
01EE& A4 C6       1284            AND   #TLM_TYPE_MSK      ;Isolate real time uplink type
01F0& AA 01       1285            ORA   #IDLE_UPLINK       ;Set uplink idle bit and save as current type
01F2& B7 00*      1286            STA   curr_tlm_type
01F4& B6 00*      1287            LDA   TELSTAT            ;Get current value of TELSTAT
01F6& A4 38       1288            AND   #TELSTAT_MSK       ; and mask changeable bits
01F8& BA 00*      1289            ORA   curr_tlm_type      ;Set new uplink type
01FA& B7 00*      1290            STA   TELSTAT            ;Write new TELSTAT and return
                  1291
                  1292  STT_END   RTS
                  1293        ;-------------------------------------------
                  1294        ; END;      (* SET_TLM_TYPE *)
                  1295        ;-------------------------------------------
                  1296
01FC& 81          1297        $EJECT
                  1298
```

What is claimed is:

1. A method for transmitting information encoded telemetry signals percutaneously between a medical device implanted within a human body and an external device, comprising the steps of:
   (a) formating the telemetry signal to be transmitted by establishing a frame having a predetermined time interval and at least first, second and third interval ranges within said frame, each range comprising a set of available pulse positions;
   (b) encoding said formatted telemetry signal by:
      (1) placing a synchronizing signal at a predetermined pulse position within said first interval range within said frame;
      (2) placing a frame identifier signal at a preselected pulse position within said second interval range within said frame, which pulse position signifies the type of information being transmitted;
      (3) placing a data bit signal at a preselected pulse position within said third interval range within said frame, which pulse position signifies the value of the data bit signal being transmitted; and
   (c) transmitting said formatted and encoded telemetry signal between said implanted medical device and said external device.

2. A method according to claim 1 wherein said formatting step further comprises the step of establishing a fourth interval range comprising a set of available pulse positions within said frame, and said encoding step further comprises placing a second data bit signal at a preselected pulse position, signifying the value of the data bit, within said fourth interval range of said frame.

3. A method according to claim 1 or claim 2 wherein said formatting step further comprises the step of providing a guard band interval between each of said interval ranges.

4. A method according to claim 1 or claim 2 wherein each of said encoding and transmitting steps further comprise generating a burst of radio frequency energy at a time within the respective interval range appropriate to pulse position the burst in the preselected pulse positions in order to identify the type of data and the value of the data being transmitted.

5. A method according to claim 1 or claim 2 wherein said encoding step further comprises placing a frame start signal at the start of each frame time interval.

6. Apparatus for transmitting information encoded telemetry signals percutaneously between an implantable medical device and an external device, comprising:
   (a) means for providing data bits to be transmitted and providing an identification bit signifying the type of data bits to be transmitted;
   (b) frame formatting means for defining a transmission frame of a predetermined time interval and having first, second and third interval ranges within said predetermined time interval;
   (c) clock means for providing clock signals at a preset clock interval;
   (d) means responsive to said clock signals and to said identification and data bit providing means for encoding said formatted telemetry signal further comprising means coupled to said frame defining means for generating a synchronizing signal at a certain pulse position within said first interval range of said transmission frame, generating a frame identifier signal at a certain pulse position within said second interval range of said transmission frame representative of the type of data bit to be transmitted, and generating a data signal at a certain pulse position within said third interval range of said transmission frame representative of the value of the data bit; and
   (e) means for transmitting said formatted and encoded telemetry signals between said implanted medical device and said external device.

7. The apparatus according to claim 6 wherein said formatting means further comprises means for establishing a fourth interval range comprising a set of available pulse positions within said frame, and said encoding means further comprises means for placing a second data bit signal at a preselected certain pulse position, signifying the value of the data bit, within said fourth interval range of said frame.

8. The apparatus according to claim 6 or claim 7 wherein said formatting means further comprises means for providing a guard band interval between each of said interval ranges.

9. The apparatus according to claim 6 or claim 7 wherein said encoding and transmitting means further comprise means for generating a burst of radio frequency energy at a time within the respective interval range and upon occurrence of a clock signal appropriate to pulse position the burst in said certain pulse positions in order to identify the type of data and the value of the data being transmitted.

10. An apparatus according to claim 6 or claim 7 wherein said encoding means further comprises means for placing a frame start signal at the start of each frame time interval.

11. An apparatus for transmitting the electrogram from a patient's heart from an implantable medical device to an external device, comprising:
   (a) sensing means for sensing the patient's natural heart beat and providing a time varying analog signal representative of the electrogram of the beating heart;
   (b) analog to digital conversion means responsive to said varying analog signal for periodically sampling and converting the analog value to a digital data bit;
   (c) means for storing said sampled digital values in a data buffer;
   (d) frame defining means for defining a transmission frame of a predetermined time interval and having first, second and third interval ranges within said frame;
   (e) clock means for transmitting said formatted and encoded telemetry signals between said implanted medical device and said external device;
   (f) means responsive to said clock signals and said digital bits for encoding said formatted telemetry signal further comprising means coupled to said frame defining means for generating a synchronizing signal at a certain pulse position within said first interval range, generating a frame identifier signal at a pulse position within said second interval range of said transmission frame identifying the frame to be transmitted as representative of the electrogram, generating a data signal representative of the value of the digital bit converted electrogram signal at a pulse position within said third interval range of said transmission frame as a function of the value of the digitized electrogram signal at that time; and
   (g) means for transmitting said formatted and encoded telemetry signals between said implanted medical device and said external device repetitively upon each periodic sampling of the EGM signal.

* * * * *